(12) United States Patent
Pel et al.

(10) Patent No.: US 7,527,953 B2
(45) Date of Patent: May 5, 2009

(54) **GENES FROM *PROPIONIBACTERIUM FREUDENREICHII* ENCODING ENZYMES INVOLVED IN VITAMIN $B_{12}$ BIOSYNTHESIS**

(75) Inventors: Herman Jan Pel, Almere (NL); Sylvia Hopper, München (DE)

(73) Assignee: DSM IP Assets B.V., Heerlen (NL)

( * ) Notice: Subject to any disclaimer, the term of this patent is extended or adjusted under 35 U.S.C. 154(b) by 220 days.

(21) Appl. No.: 10/522,389

(22) PCT Filed: Jul. 25, 2003

(86) PCT No.: PCT/EP03/08216

§ 371 (c)(1),
(2), (4) Date: Jan. 25, 2005

(87) PCT Pub. No.: WO2004/011635

PCT Pub. Date: Feb. 5, 2004

(65) Prior Publication Data

US 2006/0183188 A1      Aug. 17, 2006

(30) Foreign Application Priority Data

Jul. 25, 2002   (EP)  ................... 02255203

(51) Int. Cl.
C12N 9/12   (2006.01)
C12Q 1/58   (2006.01)
C07H 21/04  (2006.01)

(52) U.S. Cl. .................. 435/193; 435/15; 536/23.2

(58) Field of Classification Search .......... 435/15, 435/193; 536/23.2
See application file for complete search history.

(56) References Cited

FOREIGN PATENT DOCUMENTS

| | | |
|---|---|---|
| EP | 0 096 430 | 12/1983 |
| EP | 0 134 048 | 3/1985 |
| EP | 0 184 483 | 6/1986 |
| EP | 0 253 455 | 1/1988 |
| EP | 0 284 603 | 10/1988 |
| EP | 0 301 670 | 2/1989 |
| EP | 0 635 574 | 1/1995 |
| WO | WO-91/11518 | 8/1991 |
| WO | WO-97/43421 | 11/1997 |
| WO | WO-98/04726 | 2/1998 |
| WO | WO-98/06868 | 2/1998 |
| WO | WO-98/30707 | 7/1998 |
| WO | WO-98/46772 | 10/1998 |
| WO | WO-99/32617 | 7/1999 |
| WO | WO-99/67356 | 12/1999 |
| WO | WO-01/19993 | 3/2001 |

OTHER PUBLICATIONS

Blanche et al., Angew. Chem. Int. Ed. Engl. (1995) 34:383-411.
Cameron et al., J. Bacteriol. (1989) 171:547-557.
Cole et al., Nature (1998) 393:537-544.
Database EMBL 'Online,' May 2, 2001, Fleischmann et al., Accession No. AE007116 XP002217287.
Database EMBL 'Online,' Jul. 5, 2002, Accession No. A30215.
International Search Report for PCT/EP03/08216, mailed on Dec. 22, 2003, 6 pages.
Pollich et al., J. of Bacteriology (1995) 177:4481-4487.
Roessner et al., Microbiology (2002) 148:1845-1853.
Sattler et al., J. of Bacteriology (1995) 177:1564-1569.

*Primary Examiner*—Tekchand Saidha
(74) *Attorney, Agent, or Firm*—Nixon & Vanderhye P.C.

(57) ABSTRACT

Four new genes, and the enzymes that they encode, are disclosed, which are present in *Propionibacterium freudenreichii*, and which are involved in at least five steps in the biosynthetic pathway of vitamin $B_{12}$. The four enzymes are: A: cobyrinic acid a, c-diamide synthase; B: a bifunctional enzyme, which is a cobinamide kinase and a cobinamide phosphate guanyl transferase; C: a cobalamin 5-phosphate synthase; and D: an adenosyl transferase. Genes encoding the four enzymes can be placed in *Propionibacteria* shuttle vectors and used to transform *Propionibacteria* hosts, in order to improve the production of vitamin $B_{12}$ or a precursor thereof on an industrial scale during fermentation.

27 Claims, No Drawings

```
                        SEQUENCE LISTING

<160> NUMBER OF SEQ ID NOS: 17

<210> SEQ ID NO 1
<211> LENGTH: 2586
<212> TYPE: DNA
<213> ORGANISM: Propionibacterium freudenreichii
<220> FEATURE:
<221> NAME/KEY: CDS
<222> LOCATION: (1)..(2586)
<223> OTHER INFORMATION:

<400> SEQUENCE: 1 atg gtg acg gcg acg gct ctt ccg cgg gtg ctc atc gcg gcc ccc gcg      48
Met Val Thr Ala Thr Ala Leu Pro Arg Val Leu Ile Ala Ala Pro Ala
1               5                   10                  15 tcc agc cag gga aag acc acc gtg gcc atc ggc ctg atg gcg gcc ctg      96
Ser Ser Gln Gly Lys Thr Thr Val Ala Ile Gly Leu Met Ala Ala Leu
                20                  25                  30 cgg gcc tcg ggg cgc agc gtg gcc gga ttc aag gtg ggc ccc gac tac     144
Arg Ala Ser Gly Arg Ser Val Ala Gly Phe Lys Val Gly Pro Asp Tyr
            35                  40                  45 atc gat ccg ggc tat cac gca ctg gcc tgc ggt cgc ccc ggc cgc aac     192
Ile Asp Pro Gly Tyr His Ala Leu Ala Cys Gly Arg Pro Gly Arg Asn
        50                  55                  60 ctg gat ccc tat ttg tgc ggg ccc gag cgc att gcg ccg ttg ttc gcc     240
Leu Asp Pro Tyr Leu Cys Gly Pro Glu Arg Ile Ala Pro Leu Phe Ala
65                  70                  75                  80 cat ggc gcg ctg cat ccc gaa ccc gcg gac atc tcg gtc gtc gaa ggc     288
His Gly Ala Leu His Pro Glu Pro Ala Asp Ile Ser Val Val Glu Gly
                85                  90                  95 gtg atg ggc atg ttc gac ggc aag ctc ggc gcg tgg ccc gac ggc acc     336
Val Met Gly Met Phe Asp Gly Lys Leu Gly Ala Trp Pro Asp Gly Thr
                100                 105                 110 gat gac ccc gcc ggt ttt ggc tca tcg gcc cat atc gcc agg ctg ctc     384
Asp Asp Pro Ala Gly Phe Gly Ser Ser Ala His Ile Ala Arg Leu Leu
            115                 120                 125 gat gcc ccc gtg ctg ctc gtg gtc gac ggc tca cac agt gcc cgt acc     432
Asp Ala Pro Val Leu Leu Val Val Asp Gly Ser His Ser Ala Arg Thr
        130                 135                 140 gcc gca gcc ctg tgc cat ggc ctg gcc agc tac gat ccc cgc atc cat     480
Ala Ala Ala Leu Cys His Gly Leu Ala Ser Tyr Asp Pro Arg Ile His
145                 150                 155                 160 gtg gcc ggc gtc atc ctc aat cgg gtg atg ggt gcc cgc gtg gtc gac     528
Val Ala Gly Val Ile Leu Asn Arg Val Met Gly Ala Arg Val Val Asp
                165                 170                 175 gag atc acc cgg ggc tgc gca cgt gtc ggc ctg ccg gtg ctg ggg gct     576
Glu Ile Thr Arg Gly Cys Ala Arg Val Gly Leu Pro Val Leu Gly Ala
                180                 185                 190 ctg ccg aaa agc acg cgg gtg gcc gtg ggc tca cgc cac ctg gga ctg     624
Leu Pro Lys Ser Thr Arg Val Ala Val Gly Ser Arg His Leu Gly Leu
            195                 200                 205 gtc acg gcc gac gag cag ggt gac gcg atc ggc atc gtg cag cag gcc     672
Val Thr Ala Asp Glu Gln Gly Asp Ala Ile Gly Ile Val Gln Gln Ala
        210                 215                 220 ggt gag ctc gtc gcc gca cac ctc gac ctc gac gcc atc gcc acg atc     720
Gly Glu Leu Val Ala Ala His Leu Asp Leu Asp Ala Ile Ala Thr Ile
225                 230                 235                 240
```

```
gcc ggt ggg gcc cct gac ctg gcc gtc gat ccc tgg gat ccc gcc gca      768
Ala Gly Gly Ala Pro Asp Leu Ala Val Asp Pro Trp Asp Pro Ala Ala
            245                 250                 255 gag gtc gaa ccg gta ccg ggg cgt ccg gtc atc gcc atg gcc tcg ggt      816
Glu Val Glu Pro Val Pro Gly Arg Pro Val Ile Ala Met Ala Ser Gly
        260                 265                 270 ccc gca ttc acc ttc cgg tac acc gaa acc gca gaa ctg ctg gag gcg      864
Pro Ala Phe Thr Phe Arg Tyr Thr Glu Thr Ala Glu Leu Leu Glu Ala
    275                 280                 285 gcc ggc tgc cgg gtg acg gcc ttc gat ccg ctc acc gcc cgg ggc ctt      912
Ala Gly Cys Arg Val Thr Ala Phe Asp Pro Leu Thr Ala Arg Gly Leu
290                 295                 300 ccg gcc gat gtg tcc ggc ctg tac ctg ggg ggt ggt ttc ccc gag gag      960
Pro Ala Asp Val Ser Gly Leu Tyr Leu Gly Gly Gly Phe Pro Glu Glu
305                 310                 315                 320 cac gcc gag gcg ctc gcc ggc aac acc tcc ctg ggc gct gaa atc gcc     1008
His Ala Glu Ala Leu Ala Gly Asn Thr Ser Leu Gly Ala Glu Ile Ala
                325                 330                 335 tca cgc gtg tcc gag ggc ctg ccg acg gtg gcc gag tgt gcg ggg ctg     1056
Ser Arg Val Ser Glu Gly Leu Pro Thr Val Ala Glu Cys Ala Gly Leu
            340                 345                 350 ctc tac ctg tgc cgc agc ctg gat gga ctg gcg atg gcc ggg gtg gtc     1104
Leu Tyr Leu Cys Arg Ser Leu Asp Gly Leu Ala Met Ala Gly Val Val
        355                 360                 365 gac gcc gac tcg tcc atg acg ccg cgc ctg acc atc ggc tac cac cac     1152
Asp Ala Asp Ser Ser Met Thr Pro Arg Leu Thr Ile Gly Tyr His His
    370                 375                 380 gcc cgc gcc gcc aac gac agc ttc ctg atg cgc gcc ggg gag cgc tat     1200
Ala Arg Ala Ala Asn Asp Ser Phe Leu Met Arg Ala Gly Glu Arg Tyr
385                 390                 395                 400 cgg gcc cat gag ttc cac cgc acc acc ctg gac acg ccc ccc tac gac     1248
Arg Ala His Glu Phe His Arg Thr Thr Leu Asp Thr Pro Pro Tyr Asp
                405                 410                 415 cgc gac ccc gga cca caa cgg ctg ggc gac caa cgg ttg gcg tgg gac     1296
Arg Asp Pro Gly Pro Gln Arg Leu Gly Asp Gln Arg Leu Ala Trp Asp
            420                 425                 430 gtg gag acc ccg acg ggg ggc aac cga ccc gag ggg gtg ctg gtc gcc     1344
Val Glu Thr Pro Thr Gly Gly Asn Arg Pro Glu Gly Val Leu Val Ala
        435                 440                 445 ccg acc ccc ggt tcc gcg ccc agc gtc cac gcc tcc tac cag cac ctg     1392
Pro Thr Pro Gly Ser Ala Pro Ser Val His Ala Ser Tyr Gln His Leu
    450                 455                 460 cac tgg gca ggg agt ccg gta ctg gcg caa cgc ttc gcc cgg gcg gcg     1440
His Trp Ala Gly Ser Pro Val Leu Ala Gln Arg Phe Ala Arg Ala Ala
465                 470                 475                 480 agc gaa tat ggg cac acc ggc cat cac tcc ccc cgg cct gcc gcc acg     1488
Ser Glu Tyr Gly His Thr Gly His His Ser Pro Arg Pro Ala Ala Thr
                485                 490                 495 acg ccg gga gat gcg ttg tcc gca gcg ccc gac ctc acc cat cac ggg     1536
Thr Pro Gly Asp Ala Leu Ser Ala Ala Pro Asp Leu Thr His His Gly
            500                 505                 510 gat cgc gat gtg ctg ccc ggc ctg gtc gac ttg gcg gtg aac gtg cgc     1584
Asp Arg Asp Val Leu Pro Gly Leu Val Asp Leu Ala Val Asn Val Arg
        515                 520                 525 gat gtg cga cct ccg gcc tgg ctc gtg gag cgc atc gtc gcc tcc agc     1632
Asp Val Arg Pro Pro Ala Trp Leu Val Glu Arg Ile Val Ala Ser Ser
    530                 535                 540 gac cag tgg gcc cac tac ccc gat cag cgc gaa gcg acc cgt gcg gtg     1680
Asp Gln Trp Ala His Tyr Pro Asp Gln Arg Glu Ala Thr Arg Ala Val
```

```
                                    -continued
545                 550                 555                 560
gca ctg cgc cat ggc gtc aac ccc gac cag gta ctg ctc acg gcc ggg     1728
Ala Leu Arg His Gly Val Asn Pro Asp Gln Val Leu Leu Thr Ala Gly
            565                 570                 575 tcc tcg gag gcg ttc agc ctg atc gcc cac ggg ttc tcc ccg cgc tgg     1776
Ser Ser Glu Ala Phe Ser Leu Ile Ala His Gly Phe Ser Pro Arg Trp
                580                 585                 590 gcg gtc gtg gtg cat ccc cag ttc acc gaa cca gag gtg gcc ctg cgc     1824
Ala Val Val Val His Pro Gln Phe Thr Glu Pro Glu Val Ala Leu Arg
            595                 600                 605 aac gcc ggg cgc ccg gtc ggc cgc ctg gtg ctc cat gcc tcg gat ggc     1872
Asn Ala Gly Arg Pro Val Gly Arg Leu Val Leu His Ala Ser Asp Gly
        610                 615                 620 ttc cag ttc gat cac gaa ctg ctg gac ccc agg gcc gac atg gtg gtc     1920
Phe Gln Phe Asp His Glu Leu Leu Asp Pro Arg Ala Asp Met Val Val
625                 630                 635                 640 atc ggc aat ccg acc aat ccc acc ggc gtg ctg cat tcg gcg gcg agc     1968
Ile Gly Asn Pro Thr Asn Pro Thr Gly Val Leu His Ser Ala Ala Ser
                645                 650                 655 ctg cgc gcg ttg tgc cgg ccc gga cgc gtg gtg gtg gtt gac gag gca     2016
Leu Arg Ala Leu Cys Arg Pro Gly Arg Val Val Val Val Asp Glu Ala
            660                 665                 670 ttc atg gac gcc gtg ccg ggc gag ccc gag agc ctc atc ggg gca cgc     2064
Phe Met Asp Ala Val Pro Gly Glu Pro Glu Ser Leu Ile Gly Ala Arg
        675                 680                 685 atg gat ggc ctg ttg gtc acc cgc tcg ttc acg aag act tgg agc gtc     2112
Met Asp Gly Leu Leu Val Thr Arg Ser Phe Thr Lys Thr Trp Ser Val
690                 695                 700 ccg ggg ctg cgg atc gga tat gtg gtc ggg gat ccc gcg ctc att cgc     2160
Pro Gly Leu Arg Ile Gly Tyr Val Val Gly Asp Pro Ala Leu Ile Arg
705                 710                 715                 720 gtc ctg gcg cac gaa cag ccc tgt tgg ccc atc tcc acc ccc gcc ctg     2208
Val Leu Ala His Glu Gln Pro Cys Trp Pro Ile Ser Thr Pro Ala Leu
                725                 730                 735 gtc acc gcc cgc gaa tgc tcc acg cca cgc gcc gtg gag cag gcc acc     2256
Val Thr Ala Arg Glu Cys Ser Thr Pro Arg Ala Val Glu Gln Ala Thr
            740                 745                 750 tca gat gcc cga cag gcg gcg cag gac cgc cga cac ctg gtg gcc cgc     2304
Ser Asp Ala Arg Gln Ala Ala Gln Asp Arg Arg His Leu Val Ala Arg
        755                 760                 765 ctg gcc ggg atc ggc atc cag acc gtc ggg gag gcc agg gcc ccc ttc     2352
Leu Ala Gly Ile Gly Ile Gln Thr Val Gly Glu Ala Arg Ala Pro Phe
    770                 775                 780 gtc cta gtc gac ctg cgc gcc cac ccg ccc ggt ggg ctt cgt gcg gga     2400
Val Leu Val Asp Leu Arg Ala His Pro Pro Gly Gly Leu Arg Ala Gly
785                 790                 795                 800 ttg cgg acg ctc ggc ttc acc gtg cgc agc ggc gag agc ttc ccc ggc     2448
Leu Arg Thr Leu Gly Phe Thr Val Arg Ser Gly Glu Ser Phe Pro Gly
                805                 810                 815 ctg ggc gcg ggc tgg ttg cgg ctc gcg gtt cgc cac ccg gac atc agc     2496
Leu Gly Ala Gly Trp Leu Arg Leu Ala Val Arg His Pro Asp Ile Ser
            820                 825                 830 gac gcg ttc gtc gct gcc ctg gcc cgc acc atc gac gca ctg gac aca     2544
Asp Ala Phe Val Ala Ala Leu Ala Arg Thr Ile Asp Ala Leu Asp Thr
        835                 840                 845 gcg cag cac ccc atg cga cca cca caa gga gac atc aga tga             2586
Ala Gln His Pro Met Arg Pro Pro Gln Gly Asp Ile Arg
    850                 855                 860
```

<210> SEQ ID NO 2
<211> LENGTH: 861
<212> TYPE: PRT
<213> ORGANISM: Propionibacterium freudenreichii

<400> SEQUENCE: 2

Met Val Thr Ala Thr Ala Leu Pro Arg Val Leu Ile Ala Ala Pro Ala
1               5                   10                  15

Ser Ser Gln Gly Lys Thr Thr Val Ala Ile Gly Leu Met Ala Ala Leu
            20                  25                  30

Arg Ala Ser Gly Arg Ser Val Ala Gly Phe Lys Val Gly Pro Asp Tyr
        35                  40                  45

Ile Asp Pro Gly Tyr His Ala Leu Ala Cys Gly Arg Pro Gly Arg Asn
    50                  55                  60

Leu Asp Pro Tyr Leu Cys Gly Pro Glu Arg Ile Ala Pro Leu Phe Ala
65                  70                  75                  80

His Gly Ala Leu His Pro Glu Pro Ala Asp Ile Ser Val Val Glu Gly
                85                  90                  95

Val Met Gly Met Phe Asp Gly Lys Leu Gly Ala Trp Pro Asp Gly Thr
            100                 105                 110

Asp Asp Pro Ala Gly Phe Gly Ser Ser Ala His Ile Ala Arg Leu Leu
        115                 120                 125

Asp Ala Pro Val Leu Leu Val Asp Gly Ser His Ser Ala Arg Thr
    130                 135                 140

Ala Ala Ala Leu Cys His Gly Leu Ala Ser Tyr Asp Pro Arg Ile His
145                 150                 155                 160

Val Ala Gly Val Ile Leu Asn Arg Val Met Gly Ala Arg Val Val Asp
                165                 170                 175

Glu Ile Thr Arg Gly Cys Ala Arg Val Gly Leu Pro Val Leu Gly Ala
            180                 185                 190

Leu Pro Lys Ser Thr Arg Val Ala Val Gly Ser Arg His Leu Gly Leu
        195                 200                 205

Val Thr Ala Asp Glu Gln Gly Asp Ala Ile Gly Ile Val Gln Gln Ala
    210                 215                 220

Gly Glu Leu Val Ala Ala His Leu Asp Leu Asp Ala Ile Ala Thr Ile
225                 230                 235                 240

Ala Gly Gly Ala Pro Asp Leu Ala Val Asp Pro Trp Asp Pro Ala Ala
                245                 250                 255

Glu Val Glu Pro Val Pro Gly Arg Pro Val Ile Ala Met Ala Ser Gly
            260                 265                 270

Pro Ala Phe Thr Phe Arg Tyr Thr Glu Thr Ala Glu Leu Leu Glu Ala
        275                 280                 285

Ala Gly Cys Arg Val Thr Ala Phe Asp Pro Leu Thr Ala Arg Gly Leu
    290                 295                 300

Pro Ala Asp Val Ser Gly Leu Tyr Leu Gly Gly Phe Pro Glu Glu
305                 310                 315                 320

His Ala Glu Ala Leu Ala Gly Asn Thr Ser Leu Gly Ala Glu Ile Ala
                325                 330                 335

Ser Arg Val Ser Glu Gly Leu Pro Thr Val Ala Glu Cys Ala Gly Leu
            340                 345                 350

Leu Tyr Leu Cys Arg Ser Leu Asp Gly Leu Ala Met Ala Gly Val Val
        355                 360                 365

Asp Ala Asp Ser Ser Met Thr Pro Arg Leu Thr Ile Gly Tyr His His
    370                 375                 380

```
Ala Arg Ala Ala Asn Asp Ser Phe Leu Met Arg Ala Gly Glu Arg Tyr
385                 390                 395                 400

Arg Ala His Glu Phe His Arg Thr Thr Leu Asp Thr Pro Pro Tyr Asp
            405                 410                 415

Arg Asp Pro Gly Pro Gln Arg Leu Gly Asp Gln Arg Leu Ala Trp Asp
        420                 425                 430

Val Glu Thr Pro Thr Gly Gly Asn Arg Pro Glu Gly Val Leu Val Ala
            435                 440                 445

Pro Thr Pro Gly Ser Ala Pro Ser Val His Ala Ser Tyr Gln His Leu
        450                 455                 460

His Trp Ala Gly Ser Pro Val Leu Ala Gln Arg Phe Ala Arg Ala Ala
465                 470                 475                 480

Ser Glu Tyr Gly His Thr Gly His His Ser Pro Arg Pro Ala Ala Thr
                485                 490                 495

Thr Pro Gly Asp Ala Leu Ser Ala Ala Pro Asp Leu Thr His His Gly
            500                 505                 510

Asp Arg Asp Val Leu Pro Gly Leu Val Asp Leu Ala Val Asn Val Arg
        515                 520                 525

Asp Val Arg Pro Pro Ala Trp Leu Val Glu Arg Ile Val Ala Ser Ser
        530                 535                 540

Asp Gln Trp Ala His Tyr Pro Asp Gln Arg Glu Ala Thr Arg Ala Val
545                 550                 555                 560

Ala Leu Arg His Gly Val Asn Pro Asp Gln Val Leu Leu Thr Ala Gly
                565                 570                 575

Ser Ser Glu Ala Phe Ser Leu Ile Ala His Gly Phe Ser Pro Arg Trp
            580                 585                 590

Ala Val Val Val His Pro Gln Phe Thr Glu Pro Glu Val Ala Leu Arg
        595                 600                 605

Asn Ala Gly Arg Pro Val Gly Arg Leu Val Leu His Ala Ser Asp Gly
        610                 615                 620

Phe Gln Phe Asp His Glu Leu Leu Asp Pro Arg Ala Asp Met Val Val
625                 630                 635                 640

Ile Gly Asn Pro Thr Asn Pro Thr Gly Val Leu His Ser Ala Ala Ser
                645                 650                 655

Leu Arg Ala Leu Cys Arg Pro Gly Arg Val Val Val Asp Glu Ala
            660                 665                 670

Phe Met Asp Ala Val Pro Gly Glu Pro Glu Ser Leu Ile Gly Ala Arg
        675                 680                 685

Met Asp Gly Leu Leu Val Thr Arg Ser Phe Thr Lys Thr Trp Ser Val
690                 695                 700

Pro Gly Leu Arg Ile Gly Tyr Val Val Gly Asp Pro Ala Leu Ile Arg
705                 710                 715                 720

Val Leu Ala His Glu Gln Pro Cys Trp Pro Ile Ser Thr Pro Ala Leu
                725                 730                 735

Val Thr Ala Arg Glu Cys Ser Thr Pro Arg Ala Val Glu Gln Ala Thr
            740                 745                 750

Ser Asp Ala Arg Gln Ala Ala Gln Asp Arg Arg His Leu Val Ala Arg
        755                 760                 765

Leu Ala Gly Ile Gly Ile Gln Thr Val Gly Glu Ala Arg Ala Pro Phe
        770                 775                 780

Val Leu Val Asp Leu Arg Ala His Pro Pro Gly Gly Leu Arg Ala Gly
785                 790                 795                 800

Leu Arg Thr Leu Gly Phe Thr Val Arg Ser Gly Glu Ser Phe Pro Gly
```

```
                      805                 810                 815
Leu Gly Ala Gly Trp Leu Arg Leu Ala Val Arg His Pro Asp Ile Ser
                820                 825                 830

Asp Ala Phe Val Ala Ala Leu Ala Arg Thr Ile Asp Ala Leu Asp Thr
            835                 840                 845

Ala Gln His Pro Met Arg Pro Pro Gln Gly Asp Ile Arg
        850                 855                 860

<210> SEQ ID NO 3
<211> LENGTH: 657
<212> TYPE: DNA
<213> ORGANISM: Propionibacterium freudenreichii
<220> FEATURE:
<221> NAME/KEY: CDS
<222> LOCATION: (1)..(657)
<223> OTHER INFORMATION:

<400> SEQUENCE: 3 atg gac gtt cct gac agt ccc gag tcc cga agg ctg ctc gat cag ctg       48
Met Asp Val Pro Asp Ser Pro Glu Ser Arg Arg Leu Leu Asp Gln Leu
 1               5                  10                  15 tca ggc ctc ggt gcc cgg caa cgt ccg gca cga acc ctc gtc acc ggg       96
Ser Gly Leu Gly Ala Arg Gln Arg Pro Ala Arg Thr Leu Val Thr Gly
             20                  25                  30 ggc gcc cgg agc ggg aag tcc agc tat gcc gag gcg ctg ctg ggg tcg      144
Gly Ala Arg Ser Gly Lys Ser Ser Tyr Ala Glu Ala Leu Leu Gly Ser
         35                  40                  45 ttc gac cac gtc gac tac atc gcc acc tcg caa cgc aac cct gac gac      192
Phe Asp His Val Asp Tyr Ile Ala Thr Ser Gln Arg Asn Pro Asp Asp
     50                  55                  60 ccc gag tgg atg gcc cgc atc gcc gcc cac gtc gcg cgc cgc ccg aag      240
Pro Glu Trp Met Ala Arg Ile Ala Ala His Val Ala Arg Arg Pro Lys
 65                  70                  75                  80 agc tgg aac acc gtg gag acc ctt gac gtg gcg cag gtg ctg tcc gac      288
Ser Trp Asn Thr Val Glu Thr Leu Asp Val Ala Gln Val Leu Ser Asp
                 85                  90                  95 gac ggc tcc ccc gcc ctg gtc gat tgc ctg ggc gtg tgg ctc acc cgc      336
Asp Gly Ser Pro Ala Leu Val Asp Cys Leu Gly Val Trp Leu Thr Arg
            100                 105                 110 gag ctg gac gtc acc gac gcc tgg cag cac ccg gag cag gcc cgc ccc      384
Glu Leu Asp Val Thr Asp Ala Trp Gln His Pro Glu Gln Ala Arg Pro
        115                 120                 125 gag ctg cag cac cgc atc gat gag ttg gcc act gcg gtc gcc ggc tcc      432
Glu Leu Gln His Arg Ile Asp Glu Leu Ala Thr Ala Val Ala Gly Ser
    130                 135                 140 ccg cgc cgc gtg gtg ctg gtc acc aac gag gtc ggt tcc ggc gtg gtg      480
Pro Arg Arg Val Val Leu Val Thr Asn Glu Val Gly Ser Gly Val Val
145                 150                 155                 160 ccc gcc acg cag gca ggg cgc acc ttc cgt gac tgg ctg gga atc ctc      528
Pro Ala Thr Gln Ala Gly Arg Thr Phe Arg Asp Trp Leu Gly Ile Leu
                165                 170                 175 aac gcc agc gtc gcg gac gcc tgc gac gag gta ctg ctg tgc gtc gcc      576
Asn Ala Ser Val Ala Asp Ala Cys Asp Glu Val Leu Leu Cys Val Ala
            180                 185                 190 gga cgg gcg ctg agc ctg cca ccg cga ccg gga ggc cct cat ggc gcc      624
Gly Arg Ala Leu Ser Leu Pro Pro Arg Pro Gly Gly Pro His Gly Ala
        195                 200                 205 ggc acg gac ccc caa ccg aag gac gcg atc tga                          657
Gly Thr Asp Pro Gln Pro Lys Asp Ala Ile
    210                 215
```

-continued

<210> SEQ ID NO 4
<211> LENGTH: 218
<212> TYPE: PRT
<213> ORGANISM: Propionibacterium freudenreichii

<400> SEQUENCE: 4

```
Met Asp Val Pro Asp Ser Pro Glu Ser Arg Arg Leu Leu Asp Gln Leu
1               5                   10                  15

Ser Gly Leu Gly Ala Arg Gln Arg Pro Ala Arg Thr Leu Val Thr Gly
            20                  25                  30

Gly Ala Arg Ser Gly Lys Ser Ser Tyr Ala Glu Ala Leu Leu Gly Ser
        35                  40                  45

Phe Asp His Val Asp Tyr Ile Ala Thr Ser Gln Arg Asn Pro Asp Asp
    50                  55                  60

Pro Glu Trp Met Ala Arg Ile Ala Ala His Val Ala Arg Arg Pro Lys
65                  70                  75                  80

Ser Trp Asn Thr Val Glu Thr Leu Asp Val Ala Gln Val Leu Ser Asp
                85                  90                  95

Asp Gly Ser Pro Ala Leu Val Asp Cys Leu Gly Val Trp Leu Thr Arg
            100                 105                 110

Glu Leu Asp Val Thr Asp Ala Trp Gln His Pro Glu Gln Ala Arg Pro
        115                 120                 125

Glu Leu Gln His Arg Ile Asp Glu Leu Ala Thr Ala Val Ala Gly Ser
    130                 135                 140

Pro Arg Arg Val Val Leu Val Thr Asn Glu Val Gly Ser Gly Val Val
145                 150                 155                 160

Pro Ala Thr Gln Ala Gly Arg Thr Phe Arg Asp Trp Leu Gly Ile Leu
                165                 170                 175

Asn Ala Ser Val Ala Asp Ala Cys Asp Glu Val Leu Leu Cys Val Ala
            180                 185                 190

Gly Arg Ala Leu Ser Leu Pro Pro Arg Pro Gly Pro His Gly Ala
        195                 200                 205

Gly Thr Asp Pro Gln Pro Lys Asp Ala Ile
    210                 215
```

<210> SEQ ID NO 5
<211> LENGTH: 780
<212> TYPE: DNA
<213> ORGANISM: Propionibacterium freudenreichii
<220> FEATURE:
<221> NAME/KEY: CDS
<222> LOCATION: (1)..(780)
<223> OTHER INFORMATION:

<400> SEQUENCE: 5

```
atg gcc acc cgc aat gga ctg ctg gct gcc tgg gga ctg ttc acg gtg     48
Met Ala Thr Arg Asn Gly Leu Leu Ala Ala Trp Gly Leu Phe Thr Val
1               5                   10                  15 ctg ccc gca ccc gtg gtg gcc gag gtg gat gag cga ctc gcc gtg cgg     96
Leu Pro Ala Pro Val Val Ala Glu Val Asp Glu Arg Leu Ala Val Arg
            20                  25                  30 gcg atc gcc tcg atg ccg tgg gtc ggc ctc gga ctg ggc ctg atc gcc    144
Ala Ile Ala Ser Met Pro Trp Val Gly Leu Gly Leu Gly Leu Ile Ala
        35                  40                  45 gga ctc ggc tgc gcc atc gtc acc gtc gcg ggg ggc ggc cag cca ctg    192
Gly Leu Gly Cys Ala Ile Val Thr Val Ala Gly Gly Gly Gln Pro Leu
    50                  55                  60 gca atc gca gca ggc ctg gca atc ctg gcc ctg tgc acc ggc ttc ctg    240
```

| | | |
|---|---|---|
| Ala Ile Ala Ala Gly Leu Ala Ile Leu Ala Leu Cys Thr Gly Phe Leu<br>65                     70                   75                  80 | | |

```
cac ctc gac gga ctc gcc gac acc gcc gac ggc ctg ggc tcc cgc aag        288
His Leu Asp Gly Leu Ala Asp Thr Ala Asp Gly Leu Gly Ser Arg Lys
                85                  90                  95 ccg gcc cac gag gcc ctg acc atc atg cgc caa tca gac atc ggg ccc        336
Pro Ala His Glu Ala Leu Thr Ile Met Arg Gln Ser Asp Ile Gly Pro
            100                 105                 110 atg ggc gtc acc gcc atc atc ctc gtg ctg gcg ttg gag atc gcg gca        384
Met Gly Val Thr Ala Ile Ile Leu Val Leu Ala Leu Glu Ile Ala Ala
        115                 120                 125 ggc ggt tca gga cac ctt gat ggc tgg cgt ggc gtc tgg ctg ctg gtg        432
Gly Gly Ser Gly His Leu Asp Gly Trp Arg Gly Val Trp Leu Leu Val
    130                 135                 140 aca atg ccc atg gtg gcg cgc gtc agc gcc ctg tcc gcc acc gga cga        480
Thr Met Pro Met Val Ala Arg Val Ser Ala Leu Ser Ala Thr Gly Arg
145                 150                 155                 160 tgg att ccg agc gcc cac aag aag ggg ttc gga gcg ctc ttc gcc gga        528
Trp Ile Pro Ser Ala His Lys Lys Gly Phe Gly Ala Leu Phe Ala Gly
                165                 170                 175 aag acg cac cct gcg acg atc gtg gtc gcc tca gtg atc gcc gcg gtg        576
Lys Thr His Pro Ala Thr Ile Val Val Ala Ser Val Ile Ala Ala Val
            180                 185                 190 atc gcc gcg ggc agt gga tgg ctg ctc ttc ggc tgg cgg gcc gcc ctc        624
Ile Ala Ala Gly Ser Gly Trp Leu Leu Phe Gly Trp Arg Ala Ala Leu
        195                 200                 205 gtg gcg gtg tgt gcc tgc ctg gcc agc tgg gtc ttc ggc gtg gcg tgg        672
Val Ala Val Cys Ala Cys Leu Ala Ser Trp Val Phe Gly Val Ala Trp
    210                 215                 220 cgc cgc cat atc ctg gcg cgg ctc gga gga ctg acc ggc gac acc ttc        720
Arg Arg His Ile Leu Ala Arg Leu Gly Gly Leu Thr Gly Asp Thr Phe
225                 230                 235                 240 ggg tcc ctg gtc gag atg agc ggc ctg gcc tat ttg ttg acc ctg gca        768
Gly Ser Leu Val Glu Met Ser Gly Leu Ala Tyr Leu Leu Thr Leu Ala
                245                 250                 255 ttg ttc gcc tga                                                        780
Leu Phe Ala <210> SEQ ID NO 6
<211> LENGTH: 259
<212> TYPE: PRT
<213> ORGANISM: Propionibacterium freudenreichii

<400> SEQUENCE: 6

Met Ala Thr Arg Asn Gly Leu Leu Ala Ala Trp Gly Leu Phe Thr Val
1               5                   10                  15

Leu Pro Ala Pro Val Val Ala Glu Val Asp Glu Arg Leu Ala Val Arg
                20                  25                  30

Ala Ile Ala Ser Met Pro Trp Val Gly Leu Gly Leu Gly Leu Ile Ala
            35                  40                  45

Gly Leu Gly Cys Ala Ile Val Thr Val Ala Gly Gly Gln Pro Leu
        50                  55                  60

Ala Ile Ala Ala Gly Leu Ala Ile Leu Ala Leu Cys Thr Gly Phe Leu
65                  70                  75                  80

His Leu Asp Gly Leu Ala Asp Thr Ala Asp Gly Leu Gly Ser Arg Lys
                85                  90                  95

Pro Ala His Glu Ala Leu Thr Ile Met Arg Gln Ser Asp Ile Gly Pro
            100                 105                 110
```

```
Met Gly Val Thr Ala Ile Ile Leu Val Leu Ala Leu Glu Ile Ala Ala
            115                 120                 125

Gly Gly Ser Gly His Leu Asp Gly Trp Arg Gly Val Trp Leu Leu Val
        130                 135                 140

Thr Met Pro Met Val Ala Arg Val Ser Ala Leu Ser Ala Thr Gly Arg
145                 150                 155                 160

Trp Ile Pro Ser Ala His Lys Lys Gly Phe Gly Ala Leu Phe Ala Gly
                165                 170                 175

Lys Thr His Pro Ala Thr Ile Val Val Ala Ser Val Ile Ala Ala Val
            180                 185                 190

Ile Ala Ala Gly Ser Gly Trp Leu Leu Phe Gly Trp Arg Ala Ala Leu
        195                 200                 205

Val Ala Val Cys Ala Cys Leu Ala Ser Trp Val Phe Gly Val Ala Trp
    210                 215                 220

Arg Arg His Ile Leu Ala Arg Leu Gly Gly Leu Thr Gly Asp Thr Phe
225                 230                 235                 240

Gly Ser Leu Val Glu Met Ser Gly Leu Ala Tyr Leu Leu Thr Leu Ala
                245                 250                 255

Leu Phe Ala

<210> SEQ ID NO 7
<211> LENGTH: 603
<212> TYPE: DNA
<213> ORGANISM: Propionibacterium freudenreichii
<220> FEATURE:
<221> NAME/KEY: CDS
<222> LOCATION: (1)..(603)
<223> OTHER INFORMATION:

<400> SEQUENCE: 7 atg agc gga tcc gcg ccg cag cgc acc gag ccg acc acc gcc gaa ctg      48
Met Ser Gly Ser Ala Pro Gln Arg Thr Glu Pro Thr Thr Ala Glu Leu
1               5                   10                  15 cgc cac cgc ccc cga ctg atc gtg aac acc ggg aac ggc aag ggc aag      96
Arg His Arg Pro Arg Leu Ile Val Asn Thr Gly Asn Gly Lys Gly Lys
            20                  25                  30 tcc acc gcc gca ttc ggc atg gga ctg cgg gcc tgg gcg cag ggc tgg     144
Ser Thr Ala Ala Phe Gly Met Gly Leu Arg Ala Trp Ala Gln Gly Trp
        35                  40                  45 tcg atc ggg gtc ttc cag ttc atc aag tcg gga cgt tgg cac acc ggc     192
Ser Ile Gly Val Phe Gln Phe Ile Lys Ser Gly Arg Trp His Thr Gly
    50                  55                  60 gag cag cag gcc tat gca cag ctc gac cag gcc cat cgg acg acc gga     240
Glu Gln Gln Ala Tyr Ala Gln Leu Asp Gln Ala His Arg Thr Thr Gly
65                  70                  75                  80 gtc ggc gga ccg gtg gaa tgg caa tca ctc gga tcc ggc tgg tcg tgg     288
Val Gly Gly Pro Val Glu Trp Gln Ser Leu Gly Ser Gly Trp Ser Trp
                85                  90                  95 ctg agg gcg acc gag ggc acc gac cag gca gcc atg gcg gcc gcg ggc     336
Leu Arg Ala Thr Glu Gly Thr Asp Gln Ala Ala Met Ala Ala Ala Gly
            100                 105                 110 tgg gcc cac gtg cgc acc ctc ctc gcc gca cag acc cac cgg ctc tac     384
Trp Ala His Val Arg Thr Leu Leu Ala Ala Gln Thr His Arg Leu Tyr
        115                 120                 125 atc ctc gac gaa ttc gcc cat gtg ctc aac aag gga tgg ctg gat gtc     432
Ile Leu Asp Glu Phe Ala His Val Leu Asn Lys Gly Trp Leu Asp Val
    130                 135                 140 gac gag gtc gct gac gac ctg gca cat cgt ccc ggc acg caa cat gtg     480
Asp Glu Val Ala Asp Asp Leu Ala His Arg Pro Gly Thr Gln His Val
```

```
                    145                 150                 155                 160
gtg atc acc gga cgc aac tgc ccc gcc gga atc atc ggg atc gcc gac                   528
Val Ile Thr Gly Arg Asn Cys Pro Ala Gly Ile Ile Gly Ile Ala Asp
                    165                 170                 175 atc gtc acg tcc atg gac aac gtc aaa cat ccc ttt ggc aag gga gaa                   576
Ile Val Thr Ser Met Asp Asn Val Lys His Pro Phe Gly Lys Gly Glu
                180                 185                 190 cga gga cag gcg ggt atc gaa tgg tga                                               603
Arg Gly Gln Ala Gly Ile Glu Trp
        195                 200

<210> SEQ ID NO 8
<211> LENGTH: 200
<212> TYPE: PRT
<213> ORGANISM: Propionibacterium freudenreichii

<400> SEQUENCE: 8

Met Ser Gly Ser Ala Pro Gln Arg Thr Glu Pro Thr Thr Ala Glu Leu
1               5                   10                  15

Arg His Arg Pro Arg Leu Ile Val Asn Thr Gly Asn Gly Lys Gly Lys
            20                  25                  30

Ser Thr Ala Ala Phe Gly Met Gly Leu Arg Ala Trp Ala Gln Gly Trp
        35                  40                  45

Ser Ile Gly Val Phe Gln Phe Ile Lys Ser Gly Arg Trp His Thr Gly
    50                  55                  60

Glu Gln Gln Ala Tyr Ala Gln Leu Asp Gln Ala His Arg Thr Thr Gly
65                  70                  75                  80

Val Gly Gly Pro Val Glu Trp Gln Ser Leu Gly Ser Gly Trp Ser Trp
                85                  90                  95

Leu Arg Ala Thr Glu Gly Thr Asp Gln Ala Ala Met Ala Ala Ala Gly
            100                 105                 110

Trp Ala His Val Arg Thr Leu Leu Ala Ala Gln Thr His Arg Leu Tyr
        115                 120                 125

Ile Leu Asp Glu Phe Ala His Val Leu Asn Lys Gly Trp Leu Asp Val
    130                 135                 140

Asp Glu Val Ala Asp Asp Leu Ala His Arg Pro Gly Thr Gln His Val
145                 150                 155                 160

Val Ile Thr Gly Arg Asn Cys Pro Ala Gly Ile Ile Gly Ile Ala Asp
                165                 170                 175

Ile Val Thr Ser Met Asp Asn Val Lys His Pro Phe Gly Lys Gly Glu
            180                 185                 190

Arg Gly Gln Ala Gly Ile Glu Trp
        195                 200

<210> SEQ ID NO 9
<211> LENGTH: 61
<212> TYPE: DNA
<213> ORGANISM: Artificial sequence
<220> FEATURE:
<223> OTHER INFORMATION: Primer

<400> SEQUENCE: 9
gggatcctct agagcatgca agcttctcga gaatcgatag atctctaagg aagctaaaat    60
g                                                                   61

<210> SEQ ID NO 10
<211> LENGTH: 31
<212> TYPE: DNA
```

<213> ORGANISM: Artificial sequence
<220> FEATURE:
<223> OTHER INFORMATION: Primer

<400> SEQUENCE: 10
cagtagatct cgacaaggag gaacccatga g         31

<210> SEQ ID NO 11
<211> LENGTH: 30
<212> TYPE: DNA
<213> ORGANISM: Artificial sequence
<220> FEATURE:
<223> OTHER INFORMATION: Primer

<400> SEQUENCE: 11
cgtaagatct cagtttcgga catggcagtg           30

<210> SEQ ID NO 12
<211> LENGTH: 24
<212> TYPE: DNA
<213> ORGANISM: Artificial sequence
<220> FEATURE:
<223> OTHER INFORMATION: Primer

<400> SEQUENCE: 12
caccaccaac atcgatgagg aaac                 24

<210> SEQ ID NO 13
<211> LENGTH: 25
<212> TYPE: DNA
<213> ORGANISM: Artificial sequence
<220> FEATURE:
<223> OTHER INFORMATION: Primer

<400> SEQUENCE: 13
tccaattggg actcagtggt cgctg                25

<210> SEQ ID NO 14
<211> LENGTH: 39
<212> TYPE: DNA
<213> ORGANISM: Artificial sequence
<220> FEATURE:
<223> OTHER INFORMATION: Primer

<400> SEQUENCE: 14
ctgatatcaa ttggaggaca tcagatgacc cgcatcgtc  39

<210> SEQ ID NO 15
<211> LENGTH: 28
<212> TYPE: DNA
<213> ORGANISM: Artificial sequence
<220> FEATURE:
<223> OTHER INFORMATION: Primer

<400> SEQUENCE: 15
ctgaattcgg ccacgtcaga tcgcgtcc             28

<210> SEQ ID NO 16
<211> LENGTH: 39
<212> TYPE: DNA
<213> ORGANISM: Artificial sequence
<220> FEATURE:
<223> OTHER INFORMATION: Primer

<400> SEQUENCE: 16
ctgatatcaa ttggaggaca tcagatgacc cgcatcgtc  39

```
<210> SEQ ID NO 17
<211> LENGTH: 29
<212> TYPE: DNA
<213> ORGANISM: Artificial sequence
<220> FEATURE:
<223> OTHER INFORMATION: Primer

<400> SEQUENCE: 17
ctgaattccg gcggctcagg cgaacaatg                                          29
```

GENES FROM *PROPIONIBACTERIUM FREUDENREICHII* ENCODING ENZYMES INVOLVED IN VITAMIN $B_{12}$ BIOSYNTHESIS

CROSS REFERENCE TO RELATED APPLICATIONS

This application is the national phase of PCT application PCT/EP03/08216 having an international filing date of 25 Jul. 2003, which claims priority from European application 02255203.8 filed 25 Jul. 2002. The contents of these documents are incorporated herein by reference.

FIELD OF INVENTION

This invention relates to genes and the proteins (such as enzymes) involved in the biosynthetic pathway of vitamin $B_{12}$. In particular, the invention provides four novel genes (and their corresponding encoded enzymes), all derived from *Propionibacteria*, in particular *Propionibacterium freudenreichii*. These enzymes are either synthases or transferases, and can be used in the manufacture of vitamin $B_{12}$.

INTRODUCTION

Vitamin $B_{12}$ is an important vitamin for humans and animals. It is an essential vitamin, and is obtained from foodstuffs in the human and animal diet. Vitamin $B_{12}$ is naturally found in animal foods including fish, milk and milk products, eggs, meat and poultry. Certain foodstuffs, for example breakfast cereals, are fortified in vitamin $B_{12}$, and provide a particularly valuable source of the vitamin for vegetarians. Vitamin $B_{12}$ is used to treat pernicious anaemia and peripheral neuritis, and is also used as a supplement to animal feeds.

The term vitamin $B_{12}$ is used to describe compounds of the cobalt corrinoid family, in particular those of the cobalamin group. The most referred to compound of this group is cyanocobalamin and as such the term vitamin $B_{12}$ is sometimes used to refer to cyanocobalamin. In this specification the term vitamin $B_{12}$ should be attributed its broad meaning so as to include all the cobalt corrinoids of the cobalamin group, which include in particular cyanocobalamin, hydroxocobalamin, methylcobalamin and 5'-desoxyadenosylcobalamin characterised by a cyano, hydroxyl, methyl or 5'-desoxyadenosyl radical respectively.

Vitamin $B_{12}$ is produced industrially by microbial fermentation, especially using *Pseudomonas denitrificans*. However, current production levels of vitamin $B_{12}$ do not always enable cost-effective production of vitamin $B_{12}$. To increase vitamin $B_{12}$ productivity, efforts need to be made to improve the fermentation process.

The biosynthetic pathway of vitamin $B_{12}$ in *Pseudomonas denitrificans* has been well characterized[24]. This has elucidated most of the pathway[25]. A total of 22 enzymes were purified, and 22 cob genes have been identified. The role of some of these genes however is still unknown. It is thought that a closely related, but somewhat different pathway, operates in *Propionibacterium shermanii*.

In addition, workers have studied the cobalamine by synthetic pathway in *Salmonella typhimurium*. The *S. typhimurium* cob operon was isolated and cloned into *E. coli,* and that approach gave the new host the ability to make cobalamins de novo, an ability which did not previously exist. In terms of patent publications, Blanche of Rhone Poulenc Rorer is referred to concerning biosynthesis methods enabling the preparation of cobalamins.

A total of 14 genes, encoding enzymes responsible for 17 steps of the anaerobic B12 pathway in *Propionibacterium freudenreichii,* have been proposed[41]. However, this document does not give any sequences, and expresses only two gene products, allegedly causing methylation. They are expressed in *E. coli,* and there is no disclosed use of these genes to actually produce vitamin $B_{12}$.

While vitamin $B_{12}$ has been produced industrially using *Propionibacterium* species, the yields and production levels are not entirely satisfactory, and there is room for improvement. Therefore, research has been undertaken to elucidate the biosynthetic pathway in *Propionibacterium freudenreichii,* and as a result four different genes and enzymes, of the present invention, have been identified. This allows improvements in vitamin $B_{12}$ yield on an industrial scale.

SUMMARY OF THE INVENTION

Novel enzymes are now provided which are involved in the biosynthesis of vitamin $B_{12}$. At its broadest, the invention in a first aspect relates to a synthase or transferase from a Gram positive bacteria from the Order Actinomycetales, for example family Propionibacteriaceae, such as of the genus *Propionibacterium,* such as the species *Propionibacterium freudenreichii*. These enzymes are (e.g. amide) synthases or (e.g. phospho or nucleotidyl) transferases. Preferably they have the activity EC 6.3.1.-, 2.7.7-, 2.7.8- or 2.5.1.17.

More specifically, the present invention provides, in a first aspect, an (isolated and/or purified) synthase or transferase polypeptide comprising:
  (i) the amino acid sequence of SEQ ID No: 2, 4, 6 or 8; or
  (ii) a variant of (i) which is a synthase or transferase; or
  (iii) a fragment of (i) or (ii) which is a synthase or transferase.

According to a second aspect of the invention there is provided a polynucleotide which comprises:
  (a) the nucleic acid sequence of SEQ ID No. 1, 3, 5 or 7, or a sequence encoding a polypeptide of the invention;
  (b) a sequence which is complementary to, or which hybridises to, any sequence as defined in (a);
  (c) a fragment of any sequence in (a) or (b);
  (d) a sequence having at least 60, 65 or 70% identity to any sequence as defined in (a), (b) or (c); or
  (e) a sequence that is degenerate as a result of the genetic code to any of the sequences as defined in (a) to (d).

The invention also provides:
  an (e.g. expression) vector (third aspect) which comprises a polynucleotide of the invention and which may be capable of expressing a polypeptide of the invention;
  a host (fourth aspect), such as cell line or strain comprising a vector of the invention;
  a method of producing a polypeptide of the invention which method comprises maintaining a cell line or strain of the invention under conditions suitable for obtaining expression of the polypeptide and, if necessary, isolating the polypeptide; and
  a method of producing vitamin $B_{12}$ or a precursor thereof (fifth aspect), the method comprising contacting a substrate with a polypeptide or host cell of the invention.

BRIEF DESCRIPTION OF THE SEQUENCES

SEQ ID No. 1 is a DNA sequence of a first enzyme, an amide synthase, of the invention from *Propionibacterium freudenreichii;*

SEQ ID No. 2 is the amino acid sequence of the first enzyme (A);

SEQ ID No. 3 is a DNA sequence of a second enzyme, a (phospho and/or nucleotidyl) transferase from the same organism;

SEQ ID No. 4 is the amino acid sequence of the second enzyme (B);

SEQ ID No. 5 is a DNA sequence of a third enzyme, a transferase also from the same organism;

SEQ ID No. 6 is the amino acid sequence of the third enzyme (C);

SEQ ID No. 7 is a DNA sequence of a fourth enzyme, a (nucleotidyl) transferase also from the same organism;

SEQ ID No. 8 is the amino acid sequence of the fourth enzyme (D); and

SEQ ID Nos. 9 to 17 are primers.

DETAILED DESCRIPTION OF THE INVENTION

A. Polynucleotides

The present invention provides a (e.g. isolated and/or purified) polynucleotide encoding polypeptides of the invention. The present invention thus provides a polynucleotide, preferably encoding a synthase or transferase whose amino acid sequence is set out in SEQ ID No. 2, 4, 6 and/or 8. The present invention further provides a polynucleotide encoding a polypeptide having substantial amino acid sequence homology to the amino acid sequence set out in SEQ ID No. 2, 4, 6 and/or 8. Also included is a polynucleotide selected from:

(a) a polynucleotide comprising the nucleotide sequence set out in SEQ ID No. 1, 3, 5 and/or 7, or the complement thereof;

(b) a polynucleotide comprising a nucleotide sequence capable of (e.g. selectively) hybridising to a nucleotide sequence set out in SEQ ID No. 1, 3, 5 or 7, or a fragment thereof;

(c) a polynucleotide comprising a nucleotide sequence capable of (e.g. selectively) hybridising to the complement of the nucleotide sequence set out in SEQ ID No. 1, 3, 5 or 7, or a fragment thereof; and/or (d) a polynucleotide comprising a polynucleotide sequence that is degenerate as a result of the genetic code to a polynucleotide defined in (a), (b) or (c).

Polynucleotides may comprise 2, 3 or more sequences of the inventions for example SEQ ID Nos. 3 and 5 or 1, 3 and 5 (or variants thereof as defined in any of (b), (c) and (d) above).

A polynucleotide of the invention may also include a polynucleotide which:

(a) encodes a polypeptide having synthase or transferase activity, which polynucleotide is:

(1) the coding sequence of SEQ ID No. 1, 3, 5 or 7;

(2) a sequence which hybridises selectively to the complement of sequence defined in (1); or (3) a sequence that is degenerate as a result of the genetic code with respect to a sequence defined in (1) or (2); or (b) is a sequence complementary to a polynucleotide defined in (a).

Hybridisable Sequences

The term "capable of hybridizing" means that the target polynucleotide of the invention can hybridize to a nucleic acid used as a probe (for example the nucleotide sequence set out in SEQ. ID No. 1, 3, 5 or 7, or a fragment thereof or the complement thereof) at a level significantly above background. The invention also includes nucleotide sequences that encode for synthase or transferase or variants thereof as well as nucleotide sequences that are complementary thereto. The nucleotide sequence may be RNA or DNA and thus includes genomic DNA, synthetic DNA or cDNA). Preferably the nucleotide sequence is a DNA sequence if appropriate and, a cDNA sequence. Typically a polynucleotide of the invention comprises a contiguous sequence of nucleotides which is capable of hybridizing under selective conditions to the coding sequence or the complement of the coding sequence of SEQ ID No. 1, 3, 5 or 7, as appropriate. Such nucleotides can be synthesized according to methods well known in the art[1].

A polynucleotide of the invention can hybridize to the coding sequence or the complement of the coding sequence of SEQ ID No.1, 3, 5 or 7 (as appropriate) at a level significantly above background. Background hybridization may occur, for example, because of other cDNAs present in a cDNA library. The signal level (e.g. generated by the interaction between a polynucleotide of the invention and the coding sequence or complement of the coding sequence of SEQ ID No. 1, 3, 5 or 7) is typically at least 10 fold, preferably at least 100 fold, or as intense as interactions, between other polynucleotides and the coding sequence of SEQ ID No. 1, 3, 5 or 7. The intensity of interaction may be measured, for example, by radiolabelling the probe, e.g. with $^{32}P$. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.). Hybridization may be carried out under any suitable conditions known in the. arti and, as a guide, low stringency can be 2×SSC at 55° C., medium stringency can be 0.5 to 1.0×SSC at 60° C. and high stringency can be 0.1 or 0.2×SSC at 60° C. or higher (e.g. at 68° C.), all at 0.5% SDS.

Modifications

Polynucleotides of the invention may comprise DNA or RNA. They may be single or double stranded. They may also be polynucleotides which include within them one or more synthetic or modified nucleotides. A number of different types of modifications to polynucleotides are known in the art. These include methylphosphonate and phosphorothioate backbones and/or addition of acridine or polylysine chains at the 3' and/or 5' ends of the molecule. For the purposes of the present invention, it is to be understood that the polynucleotides described herein may be modified by any method available in the art.

It is to be understood that skilled persons may, using routine techniques, make nucleotide substitutions that do not affect the polypeptide sequence encoded by the polynucleotides of the invention to reflect the codon usage of any particular host organism, for example in which the polypeptides of the invention are to be expressed.

The coding sequence of SEQ ID No. 1, 3, 5 or 7 may be modified by nucleotide substitutions, for example from or up to 1, 2 or 3 to 10, 25, 50 or 100 substitutions. The polynucleotide may alternatively or additionally be modified by one or more insertions and/or deletions and/or by an extension at either or both ends. The modified polynucleotide generally encodes a polypeptide which has synthase or transferase activity. Degenerate substitutions may be made and/or substitutions may. be made which would result in a conservative amino acid substitution when the modified sequence is translated, for example as discussed with reference to polypeptides later.

Homologues

A nucleotide sequence which is capable of selectively hybridizing to (e.g. the complement of) the DNA coding sequence of SEQ ID No. 1, 3, 5 or 7 may have at least 50% or 60%, at least 70%, at least 80%, at least 90%, at least 95%, at least 98% or at least 99% sequence identity (or homology) to the coding sequence of SEQ.ID No. 1, 3, 5 or 7. This may be over a region of at least 20, preferably at least 30, for instance at least 40 or 50 such as at least 60 or 80, more preferably at least 100, 200, 400, 500 or even 600 contiguous nucleotides or optimally over the full length of SEQ ID No. 1, 3, 5 or 7. For individual sequences the sequence identity maybe:

(a) for SEQ ID No; 1, at least 85% or 90%;
(b) for SEQ ID No. 3, at least 70%;
(c) for SEQ ID No. 5, at least 90% or 95%; and/or
(d) for SEQ ID No. 7, at least 90%, 95% or 98%.

Any combination of the above mentioned degrees of homology and minimum sized may be used to define polynucleotides of the invention, with the more stringent combinations (i.e. higher homology over longer lengths) being preferred. Thus for example a polynucleotide which is at least 80% or 90% homologous over 25, preferably over 30 nucleotides forms one aspect of the invention, as does a polynucleotide which is at least 90% homologous over 40 nucleotides.

Homologues of polynucleotide (or protein) sequences typically have at least 70% homology, preferably at least 80, 90%, 95%, 97% or 99% homology, for example over a region of at least 15, 20, 30, 100 more contiguous nucleotides (or amino acids). The homology may calculated on the basis of amino acid identity (sometimes referred to as "hard-homology"). Identity or homology is usually calculated on the basis of the entire sequence unless otherwise specified.

For example the UWGCG Package provides the BESTFIT program which can be used to calculate homology (for example used on its default settings[5]). The PILEUP and BLAST algorithms can be used to calculate homology or line up sequences (such as identifying equivalent or corresponding sequences, for example on their default settings[6,7]).

Software for performing BLAST analyses is publicly available through the National Center for Biotechnology Information (http://www.ncbi.nln.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold[6,7]. These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BILAST program uses as defaults a word length (W) of 11, the BLOSUM62 scoring matrix[8] alignments (B) of 50, expectation (E) of 10, M=5, N=4, and a comparison of both strands.

The BLAST algorithm performs a statistical analysis of the similarity between two sequences[9]. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0. 1, more preferably less than about 0.01, and most preferably less than about 0.001.

Fragments, homologues and other variants may be at least 500 or 550 nucleotides in length (e.g. for SEQ. ID. No. 7) and may encode at least (e.g. the first) 170, 180 or 200 amino acids of the corresponding protein.

Primers and Probes

Polynucleotides of the invention include and may be used as a primer, e.g. a PCR primer, a primer for an alternative amplification reaction, a probe, or the polynucleotides may be cloned into vectors. Such primers, probes and other fragments will be at least or up to 20, for example at least 25, 30 or 40 nucleotides in length. They will typically be up to 40, 50, 60, 70, 100, 150, 200 or 300 nucleotides in length, or even up to the same number or a few nucleotides (such as 5 or 10 nucleotides) short of the coding sequence of SEQ ID No. 1, 3, 5 or 7.

In general, primers will be produced by synthetic means, involving a step-wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the synthase or transferase which it is desired to clone, bringing the primers into contact with mRNA or cDNA obtained from a target (e.g yeast, bacterial, plant, prokaryotic or fungal) cell, preferably of an a bacterial, e.g. *Propionibacterium* strain, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the synthase or transferase sequence described herein. Genomic clones corresponding to the cDNA of SEQ ID No. 1, 3, 5 or 7 or the synthase or transferase gene containing, for example, introns and promoter regions are within the invention also and may also be obtained in an analogous manner (e.g. recombinant means, PCR, cloning techniques), starting with genomic DNA from a fungal, yeast, bacterial plant or prokaryotic cell.

The polynucleotides or primers may carry a revealing label, e.g. a radioactive or non-radioactive label. Suitable labels include radioisotopes such as $^{32}P$ or $^{35}S$, enzyme labels, or other protein labels such as biotin. Such labels may be added to polynucleotides or primers of the invention and may be detected using techniques known per se.

Polynucleotides, labelled or unlabelled may be used in nucleic acid-based tests for detecting or sequencing a synthase or transferase or a variant thereof in a (e.g. bacterial) sample. Such tests for detecting generally comprise bringing a (e.g. bacterial) sample (suspected of) containing DNA into contact with a probe or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which was hybridized to the probe. Alternatively, the sample nucleic acid may be immobilized on a solid support, and the amount of probe bound to such a support can be detected.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like.

Preferably, the polynucleotide of the invention is obtainable from the same organism as the polypeptide, such as a bacteria, in particular a bacteria of the family *Mycobacteriaceae*, preferably of the genus *Propionibacterium*.

The polynucleotides of the invention also include variants of the sequence of SEQ ID No. 1, 3, 5 or 7 which have synthase or transferase activity. Variants may be formed by additions, substitutions and/or deletions and may have the ability to act as a synthase or transferase, or have the activity EC 6.3.1-, 2.7.7 (or 8).- or 2.5.1.17.

Production of Polynucleotides

Polynucleotides which do not have 100% identity with SEQ ID No. 1, 3, 5 or 7 but fall within the scope of the invention can be obtained in a number of ways. Thus variants of the sequences described herein may be obtained for example by probing genomic DNA libraries made from a range of organisms, for example those discussed as sources of the polypeptides of the invention. In addition, other bacterial or prokaryotic homologues may be obtained and such homologues and fragments thereof in general will be capable of hybridising to SEQ ID No. 1, 3, 5 or 7. Such sequences may be obtained by probing cDNA libraries or genomic DNA libraries from other species, and probing such libraries with probes comprising all or part of SEQ ID. 1, 3, 5 or 7 under conditions of medium to high stringency (as described earlier). Nucleic acid probes comprising all or part of SEQ ID No. 1, 3, 5 or 7 may be used to probe cDNA libraries from other species, such as those described as sources for the polypeptides of the invention.

Species homologues may also be obtained using degenerate PCR which will use primers designed to target sequences within the variants and homologues encoding conserved amino acid sequences. The primers can contain one or more degenerate positions and will be used at stringency conditions lower than those used for cloning sequences with single sequence primers against known sequences.

Alternatively, such polynucleotides may be obtained by site directed mutagenesis of the synthase or transferase sequences or variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The invention includes double stranded polynucleotides comprising a polynucleotide of the invention and its complement.

The present invention also provides polynucleotides encoding the polypeptides of the invention described below. Since such polynucleotides will be useful as sequences for recombinant production of polypeptides of the invention, it is not necessary for them to be capable of hybridising to the sequence of SEQ ID No. 1, 3, 5 or 7, although this will generally be desirable. Otherwise, such polynucleotides may be labelled, used, and made as described above if desired.

B. Polypeptides

The present invention relates to an (e.g. (substantially) purified and/or isolated) synthase or transferase or variant thereof as defined later. The polypeptides of the invention may consist essentially of the amino acid sequence of SEQ ID No. 2, 4, 6 or 8 or of a variant of that sequence. Polypeptides may also be encoded by a polynucleotide of the invention as described above.

A polypeptide of the invention may be in an isolated or a substantially purified form. It will be understood that the polypeptide may be mixed with carriers or diluents which will not interfere with the intended purpose and/of function of the polypeptide and still be regarded as substantially isolated. It will generally comprise the polypeptide in a preparation in which more than 20%, e.g. more than 30%, 40%, 50%, 80%, 90%, 95% or 99%, by weight of the polypeptide in the preparation is a polypeptide of the invention. Routine methods can be employed to purify and/or synthesise the proteins according to the invention[1]. For some formulations (e.g. for non-pharmaceutical uses) the amount of polypeptide present may be small, for example from 0.01 to 10%, such as from 0.1 to 5%, or 2% or even from 0.2 to 1%.

Preferably, the polypeptide of the invention is obtainable from a microorganism, for example one which possesses a gene encoding an enzyme with synthase or transferase activity. More preferably the microorganism is bacterial, such as Gram positive bacteria. The microrganism may be of the Phylum or class Actinobacteria, e.g.Subclass Adinobacteridae. Preferably the microorganism is of Order Actinomycetales, such as Sub order Propionibacterineae and optimally from the family Propionibacteriaceae. Preferred organisms are thus of the genus *Propionibacterium,* such as of the species *Propionibacterium freudenreichii*. Preferably the microorganism is capable of producing or synthesising vitamin B12.

Activity

A polypeptide of the invention can have one or more of the following features, namely it:

(1) possesses synthase or transferase activity;
(2) acts as an amide synthase or a phosphor nucleotidyl- or aryl-transferase;
(3) catalyses at least one step in the vitamin $B_{12}$ biosynthetic pathway;
(4) has an activity within EC 6.3.1-, EC 2.7.7-, EC 2.7.8- or EC 2.5.1.17;
(5) has a length of 150 or 170 to 270 or 300 amino acids or from 800 or 840 to 880 or 920 amino acids;
(6) is a cobyrinic acid -a,c-diamide synthase, a cobinamide kinase, a cobinamide phosphate guanyl transferase, a cobalamin (5'-phosphate), synthase and/or an adenosyl transferase;
(7) acts on a substrate, or produces a product, which comprises:
   (i) a corrin core or ring system;
   (ii) up to 4 aryl, optionally pyrrole, rings;
   (iii) a tetrapyrrole ring system and/or a transition metal (e.g. cobalt) atom; and/or
   (iv) an amide, phosphate, guanidyl, aryl or adenosyl moiety or group; and/or
(8) catalyses amidation, phosphorylation, nucleotidylation, arylation, ribazole or adenosyl addition and/or adenosylation.

A table of the main characteristics of the polypeptides of the invention is given below.

| Designation/reaction | DNA seq No. (length, nucs) | Protein seq No. | Seq length (amino acids) | Enzyme activity/activities | Substrate | Product (formula) | Enzyme class/type | Gene reference No. (code name) |
|---|---|---|---|---|---|---|---|---|
| A | 1 (2586) | 2 | 861 | cobyrinic acid a, c diamide synthase (EC 6.6.3.-) | Cobyrinic acid (I) | Cobyrinic a, c diamide (IB) (with intermediate cobyrinic acid c-amide, IA) | (amide) synthase | PFR 111925 (cobA/cbiA) |
| B (B1, B2) | 3 (657) | 4 | 218 | cobinamide kinase (EC 2.7.1.-) cobinamide phosphate guanyl transferase (EC 2.7.7.-) | Adenosyl cobinamide (II) Adenosyl cobinamide phosphate (IIA) | Adenosinyl cobinamide phosphate (IIA) Adenosyl-GDP-cobamide (IIB) | (phospho) transferase (nucleotidyl) transferase | PFR 111926 (cobU) |
| C | 5 (780) | 6 | 256 | cobalamin (5'-phosphate) synthase (EC 2.7.8.-) | Adenosyl-GDP-cobamide (IIB) | Adenosyl-5,6-dimethyl benzimidazolyl cobamide, (adenosyl cobalamin i.e. vitamin $B_{12}$(IIC) | (aryl) transferase | PFR 111927 (cobS) |
| D | 7 (603) | 8 | 200 | (cob(1)alamin) adenosyl transferase (EC 2.5.1.17) | Cobyrinic acid a, c diamide (IB) | Adenosyl cobyrinic acid a, c diamide(IC) | (nucleotidyl) transferase | PFR 111924 |

Variants and Homologues

A polypeptide of the invention can comprise the amino acid sequence set out in SEQ ID No. 2, 4, 6 or 8 (or a variant thereof, such as) a substantially homologous sequence or a fragment of either sequence and can have synthase or transferase activity. In general, the naturally occurring amino acid sequence shown in SEQ ID No. 2, 4, 6 or 8 is preferred.

In particular, the polypeptide of the invention may comprise:

(a) the polypeptide sequence of SEQ ID No. 2, 4, 6 or 8;

(b) a naturally occurring variant or species homolog, paralog or ortholog thereof; or (c) a protein with at least 70, at least 80, at least 90, at least 95, at least 98 or at least 99% sequence identity to (a) or (b).

A variant may be one that occurs naturally, for example in fungal, bacteria, yeast or plant cells and which can function in a substantially similar manner to the protein of SEQ ID No. 2, 4, 6 or 8, for example it has synthase or transferase activity. Similarly a species homolog of the protein will be the equivalent protein which occurs naturally in another species and which can function as a synthase or transferase enzyme. Variants include allelic variants either from the same strain as the polypeptide of the invention or from a different strain, but of the same genus, or of the same species.

Variants and species homologues can be obtained by following the procedures described herein for the production of the polypeptide of SEQ ID No. 2, 4, 6 or 8 and performing such procedures on a suitable cell source, for example a bacterial, yeast, fungal or plant cell. It will also be possible to use a probe as defined above to probe libraries made from yeast, bacterial, fungal or plant cells in order to obtain clones including the variants or species homology. The clones can be manipulated by conventional techniques to generate a polypeptide of the invention which can then be produced by recombinant or synthetic techniques known per se.

The polypeptide of the invention preferably has at least 70% sequence identity to any of the proteins of SEQ ID No. 2, 4, 6 or 8, more preferably at least 80%, at least 90%, at least 95%, at east 97% or at least 99% sequence identity thereto, for example. for each sequence over a region of at least 60, at least 100, 150, 200, 250 or 300 (or even 500, 600, 700 or 800) contiguous amino acids or over the fall length of SEQ ID No. 2, 4, 6 or 8. For individual sequences the sequence identity may be:

(a) for SEQ ID No. 2, at least 55%, 60% or 65%;

(b) for SEQ ID No. 4, at least 50%, 55% or 60%;

(c) for SEQ ID No. 6, at least 40%, 45% or 50%; and/or (d) for SEQ ID No. 8, at least 90%, 95%, 98% or 99% (e.g. over, or the sequence being longer than, at least 150, 170, 200 or 230 amino acids).

The sequence of the polypeptide of SEQ ID No. 2, 4, 6 or 8 and of variants and species homologs can thus be modified to provide polypeptides of the invention. Amino acid substitutions may be made, for example from or up to 1, 2 or 3 to 10, 20, 30, 50 or 100 substitutions. The same number of deletions and insertions may also be made. These changes may be made outside regions critical to the function of the polypeptide and so may still result in an active enzyme. The modified polypeptide generally retains activity as a synthase or transferase.

Polypeptides of the invention include fragments of the above mentioned full length polypeptides and of variants thereof, including fragments of the sequence set out in SEQ ID No. 2, 4, 6 or 8. Such fragments typically retain activity as a synthase or transferase. Fragments maybe at least 50, 100, 150, 200 or 250 amino acids long or may be this number of amino acids short of the full length sequence (as shown in SEQ ID No. 2, 4, 6 or 8).

Polypeptides of the invention can if necessary be produced by synthetic means although usually they will be made recombinantly as described below. They may be modified for example by the addition of histidine residues or a T7 tag to assist their identification or purification or by the addition of a signal sequence to promote their secretion from a cell.

The term "variants" refers to polypeptides which have the same essential character or basic biological functionality as the synthase or transferase, and include allelic variants. The essential character of synthase is that it is an enzyme that exhibits EC 6.3.-.-. (e.g. EC 6.3.1.-.) activity or can add an amine group to a substrate (e.g. amidate). For a transferase, this is an enzyme that exhibits EC 2.7.-.-. (e.g. EC 2.7.7 or 8.-) or EC 2.5.-.-. (e.g. EC 2.5.1.-, such as EC 2.5.1.17) activity and can transfer a substituent or chemical moiety from one compound to another. Preferably a variant polypeptide has the same activity. A polypeptide having the same essential character as may be identified by performing a substrate degradation assay.

Variants of SEQ ID No. 2, 4, 6 or 8 also include sequences which vary from SEQ ID No. 2, 4, 6 or 8 but which are not necessarily derived from the naturally occurring enzyme. These variants may be described as having a percentage homology to SEQ ID No. 2, 4, 6 or 8 or having a number of substitutions within this sequence. Alternatively a variant may be encoded by a polynucleotide which hybridizes to SEQ ID No. 1, 3, 5 or 7.

The variants can be defined in a similar manner to the variants of SEQ ID No. 1, 3, 5 or 7. Thus the variants may comprise variant sequences derived from other bacterial strains, e.g. *Propionibacterium*. Other variants can be identified from other strains by looking for synthase or transferase. activity and cloning and sequencing as before. Variants may include the deletion, modification or addition of single amino acids or groups of amino acids within the protein sequence, as long as the peptide maintains the basic biological functionality. e.g. a synthase or transferase.

Conservative substitutions may be made, for example according to the following Table. Amilno acids in the same block in the second column and preferably in the same line in the third column may be substituted for each other. Preferably substitutions do not affect the folding or activity of the polypeptide.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Shorter polypeptide sequences are within the scope of the invention. For example, a peptide of at least 50 amino acids or up to 60, 70, 80, 100, 150, 200, 400, 500, 600 or 700 amino acids in length is considered to fall within the scope of the invention as long as it demonstrates the basic biological functionality of the synthase or transferase. In particular, but not exclusively, this aspect of the invention encompasses the situation when the protein is a fragment of the complete protein sequence and may comprise or represent a substrate binding region, cleaving and/or transferring region.

Modifications

Polypeptides of the invention may be chemically modified, e.g. post-translationally modified. For example, they may comprise modified amino acid residues. They may also be modified by the addition of histidine residues (to assist their purification) or by the addition of a signal sequence (to promote insertion into the cell membrane). The polypeptide may have one or more (N) amino- or (C) carboxyl-terminal extensions, such as an amino-terminal methionine residue, a small linker peptide of up to about 20-25 residues, or a (small) extension that facilitates purification, such as a poly-histidine or T7 tag, an antigenic epitope or a (e.g. maltose) binding domain[14] (e.g. at the C-terminus). These extensions may or may not be added via a linker.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

The polypeptide may be modified to include non-naturally occurring amino acids or to increase the stability of the polypeptide. When the peptide is produced by synthetic means, such amino acids may be introduced during production. The peptide may also be modified following either synthetic or recombinant production.

The polypeptides of the invention may also be produced using, or comprise, (one or more) D-amino acids.

A number of side chain modifications are known in the art and maybe made to the side chains of the proteins or peptides of the present invention. Such modifications include, for example, modifications of amino acids by reductive alkylation by reaction with an aldehyde followed by reduction with NaBH$_4$, amidination with methylacetimidate or acylation with acetic anhydride.

The sequences provided by the present invention may also be used as starting materials for the construction of "second generation" enzymes. "Second generation" enzymes are ones altered by mutagenesis techniques (e.g. site-directed mutagenesis), which have properties that differ from those of the wild-type or recombinant enzymes such as those produced by the present invention. For example, the temperature or pH optimum, specific activity, substrate affinity or thermostability may be altered so as to be better suited for application in a defined process.

Amino acids essential to activity, and therefore preferably subject to substitution, may be identified according to procedures known in the art, such as site-directed mutagenesis or alanine-scanning mutagenesis[10]. In the latter technique mutations are introduced at every residue in the molecule, and the resultant mutant molecules are tested for biological activity (e.g. synthase or transferase activity) to identify amino acid residues that are critical to the activity of the molecule. Sites of enzyme-substrate interaction can also be determined by analysis of crystal structure as determined by such techniques as nuclear magnetic resonance, crystallography or photo-affinity labelling[11,12,13] or molecular modelling.

The use of yeast and fungal host cells may provide any post-translational modifications (e.g. proteolytic processing, myristilation, glycosylation, truncation, and tyrosine, serine or threonine phosphorylation) influencing biological activity on recombinant expression products of the invention.

Polypeptides of the invention may be provided in a form such that they are outside their natural cellular environment. Thus, they may be substantially isolated or purified, as discussed above; or in a cell in which they do not occur in nature, e.g. a cell of other bacterial species, animals, yeast or fungi.

C. Recombinant Aspects.

The invention also provides vectors comprising a polynucleotide of the invention, including cloning and expression vectors, and methods of growing, transforming or transfecting such vectors in a suitable host cell, for example under conditions in which expression of a polypeptide of the invention occurs. Provided also are host cells comprising a polynucleotide or vector of the invention wherein the polynucleotide is heterologous to the genome of the host cell. The term "heterologous", usually with respect to the host cell, means that the polynucleotide does not naturally occur in the genome of the host cell or that the polypeptide is not naturally produced by that cell. Preferably, the host cell is a bacterial cell, for example a (e.g. Gram positive) cell of the family Propionibacteriaceae.

Polynucleotides of the invention can be incorporated into a recombinant replicable vector, for example a cloning or expression vector. The vector maybe, used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Vectors

The polynucleotide of the invention may be inserted into an expression cassette. The vector into which the expression cassette or polynucleotide of the invention is inserted may be any vector which may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

Preferably, a polynucleotide of the invention in a vector is operably linked to a regulatory sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences.

The vector may be a plasmid, cosmid, virus or phage vector, usually provided with an origin of replication, optionally a promoter for the expression of the polynucleotide and optionally an enhancer and/or a regulator of the promoter. A terminator sequence may be present, as may be a polyadenylation sequence. The vector may contain one or more selectable marker genes, for example an ampicillin resistance gene (in the case of a bacterial plasmid) or a neomycin resistance gene (for a mammalian vector). Vectors may be used in vitro, for example for the production of RNA or used to transfect or transform a host cell. They may comprise two or more polynucleotides of the invention, for example for overexpression.

The vector may comprise two, three or all four polynucleotides of the invention, in other words at least two, three or four polynucleotide sequences that encode the four polypeptides of the invention (SEQ ID Nos. 2, 4, 6 and 8, or variants (fragments or substantially homologous sequences thereof), as defined earlier). Preferred combinations include the sequences encoding protein B (cobU) and protein C (cobS), optionally with the third protein A (cobA/cbiA). Thus, the vector may comprise SEQ ID Nos. 1, 3, 5 and/or 7, or fragments thereof, or sequences that hybridize thereto, as defined earlier in the specification.

Preferably at least 2, 3 and (optimally) 4 of the polynucleotides are in the same operon, for example operon C. They may be arranged so that the vector (or eventual host) comprises an operon, or sequence, comprising sequences encoding one or more of the following enzymes, in the order: (nucleotidyl, transferase, (amide) synthase, (phospho) transferase and/or (nucleotidyl) transferase, (aryl) transferase. Thus, if all four polynucleotides are present, then the order in which they are arranged is preferably SEQ ID. Nos. 7,1,3, 5 (or variants of these sequences as previously defined).

The DNA sequence encoding the polypeptide is preferably introduced into a suitable host as part of an expression cassette (or construct) in which the DNA sequence is operably linked to expression signals which are capable of directing expression of the DNA sequence in the host cells. For transformation of the suitable host with the expression construct transformation procedures are available which are well known to the skilled person[3,4]. The expression construct can be used for transformation of the host as part of a vector carrying a selectable marker, or the expression construct may be co-transformed as a separate molecule together with the vector carrying a selectable marker. The vector may comprise one or more selectable marker genes.

Preferred selectable markers[15,16] include but are not limited to those that complement a defect in the host cell or confer resistance. to a drug. They include e.g. versatile marker genes that can be used for transformation of bacteria (e.g. *E. coli*), most filamentous fungi and yeasts such as acetamidase genes or cDNAs (the amdS, niaD,facA genes or cDNAs from *A.nidulans, A.oryzae*, or *A.niger*), or genes providing resistance to antibiotics like G418, hygromycin, bleonycin, kanamycin, phleomycin or benomyl resistance (benA). Alternatively, specific selection markers can be used such as auxotrophic markers which require corresponding mutant host strains: e.g. URA3 (from *S. cerevisiae* or analogous genes from other yeasts), pyrG or pyrA (from *A.nidulans* or *A.niger*), argB (from *A.nidulans* or *A.niger*) or trpC. In a preferred embodiment the selection marker is deleted from the transformed host cell after introduction of the expression construct so as to obtain transformed host cells capable of producing the polypeptide which are free of selection marker genes[21,22].

Other markers include ATP synthetase, subunit 9 (oliC), orotidine-5'-phosphatedecarboxylase (pvrA), the bacterial G418 resistance gene (this may also be used in yeast, but not in fungi), the ampicillin resistance gene (*E. coli*), the neomycin resistance gene (*Bacillis*) and the *E. coli* uidA gene, coding for β-glucuronidase (GUS). Vectors may be used in vitro, for example for the production of RNA or used to transfect or transform a host cell.

For most (filamentous) fungi, yeast or bacteria, the vector or expression construct is preferably integrated, such as in the genome of the host cell in order to obtain stable transformants. However, for certain yeasts also suitable episomal vectors are available into which the expression construct can be incorporated for stable and high level expression, examples thereof include vectors derived from the 2μ and pKD1 plasmids of *Saccharomyces* and *Kluyveromyces*, respectively, or vectors containing an AMA sequence (e.g. AMA1 from *Aspergillus*[3,20]). In case the expression constructs are integrated in the host cell's genome, the constructs are either integrated at random loci in the genome, or at predetermined target loci using homologous recombination, in which case the target loci preferably comprise a highly expressed gene. A highly expressed gene is a gene whose mRNA can make up at least 0.01% (w/w) of the total cellular mRNA, e.g. under induced conditions, or alternatively, a gene whose gene product can make up at least 0.2% (w/w) of the total cellular protein (or, in case of a secreted gene product, can be secreted to a level of at least 0.05 g/l). A number of examples of suitable highly expressed genes are provided below.

A vector or expression construct for a given host cell may comprise the following elements operably linked to each other in a consecutive order from the 5'-end to 3'-end relative to the coding strand of the sequence encoding the polypeptide of the first invention:

(1) a promoter sequence capable of directing transcription of the DNA sequence encoding the polypeptide in the given host cell;

(2) optionally, a signal sequence capable of directing secretion of the polypeptide from the given host cell into a culture medium;

(3) a DNA sequence encoding a mature and preferably active form of the polypeptide; and preferably also (4) a transcription termination region (terminator) capable of terminating transcription downstream of the DNA sequence encoding the polypeptide.

Downstream of the DNA sequence encoding the polypeptide there may be a 3' untranslated region containing one or more transcription termination sites (e.g. a terminator). The origin of the terminator is less critical. The terminator can e.g. be native to the DNA sequence encoding the polypeptide. However, preferably a yeast terminator is used in yeast host cells, a filamentous fingal terminator is used in filamentous fungal host cells and a bacterial terminator in bacterial cells. More preferably, the terminator is endogenous to the host cell (in which the DNA sequence encoding the polypeptide is to be expressed).

Enhanced expression of the polynucleotide encoding the polypeptide of the invention may also be achieved by the selection of heterologous regulatory regions, e.g. promoter, and/or terminator regions, which may serve to-increase expression and, if desired, secretion levels of the protein of interest from the expression host and/or to provide for the inducible control of the expression of the polypeptide of the invention.

Aside from the promoter native to the gene encoding the polypeptide of the invention, other promoters may be used to direct expression of the polypeptide of the invention. The promoter may be selected for its efficiency in directing the expression of the polypeptide of the invention in the desired expression host.

Promoters/enhancers and other expression regulation signals may be selected to be compatible with the host cell for which the expression vector is designed. For example prokaryotic promoters may be used, in particular those suitable for use in *E.coli* strains. When expression is carried out in mammalian cells, mammalian promoters may be used. Tissues-specific promoters, for example hepatocyte cell-specific promoters, may also be used. Viral promoters may also be used, for example the Moloney murine leukaemia virus long terminal repeat (MMLV LTR), promoter rous sarcoma- virus (RSV) LTR promoter, SV40 (e.g. large T antigen) promoter, human cytomegalovirus (CMV) E promoter, herpes simplex virus promoters or adenovirus promoters, HSV promoters such as the HSV IE promoters), or HPV promoters, particularly the HPV upstream regulatory region (URR).Yeast promoters include *S. cerevisiae* GAL4 and ADH promoters, the *S. pombe* nmt 1 and adh promoter. Mammalian promoters include the metallothionein promoter which may be induced in response to heavy metals such as cadmium and β-actin promoters. Tissue-specific promoters, in particular endothelial or neuronal cell specific promoters (for example the DDAHI and DDAHII promoters), are especially preferred.

A variety of promoters[15,16] can be used that are capable of directing transcription in the host cells of the invention. Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia,* respectively, the glucoamylases (glaA) genes from *A.niger* and *A.awamori,* the *A.oryzae* TAKA-amylase gene, the *A.nidulans* gpdA gene and the *T.reesei* cellobiohydrolase genes.

Examples of strong constitutive and/or inducible promoters which are preferred for use in fungal expression hosts[15,16] are those which are obtainable from the fungal genes for xylanase (xlnA), phytase, ATP-synthetase, subunit 9 (oliC), triose phosphate isomerase (tpi), alcohol dehydrogenase (AdhlA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SPo2 promoters as well as promoters from extracellular protease genes.

Promoters suitable for plant cells include napaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters. All these promoters are readily available in the art.

The vector may further include sequences flanking the polynucleotide giving rise to RNA which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors[15,19] and retroviruses, including lentiviruses, adenoviruses, adeno-associated viruses and HPV-viruses (such as HPV-16 or HPV-18). Gene transfer techniques using these viruses are known to those skilled in the art. Retrovirus vectors for example may be used to stably-integrate the polynucleotide giving rise to the antisense RNA into the host genome. Replication-defective adenovirus vectors by contrast remain episomal and therefore allow transient expression.

The vector may contain a polynucleotide of the invention oriented in an antisense direction to provide for the production of antisense RNA. This may be used to reduce, if desirable, the levels of expression of the polypeptide.

For bacteria, specialised vectors can be employed, for example an expression vector or a plasmid. Suitable vectors and expression systems for *Propionibacteria* are known in the art[27,28,30]. For example one can use a plasmid from another *Propionibacterium* species, such as *P. acidipropionici.* This plasmid can be used to prepare a shuttle vector (such as pPK705) containing one or more of the six open reading frames of the *P. acidipropionici* plasmid. The vector may contain a drug marker, such as a hygromycin B resistant gene. This vector has been able to successfully transform *Propionibacterium freudenreichii* subspecies *shermanii.* Transformation may be by electroporation.

Several promoters particularly suitable for *Propionibacterium* can be employed, in particular from *Propionibacterium freudenreichii* subspecies *shermanii.* These include the *Propionibacterium* bacterium promoters P4 and P138.

Alternatively or in addition, one may use one or more endogenous plasmids of *Propionibacterium,* or vectors derived from such a plasmid, in order to express a preferably heterologous protein in bacteria. Such plasmids and vectors are known in the art[29] and may be based on plasmids from *Propionibacterium* bacterium LMG16545 (deposited under accession nos. CBS 101022 and CBS 101023).

Host Cells and Expression

In a further aspect the invention provides a process for preparing a polypeptide according to the invention which comprises cultivating a host cell (e.g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e.g. an expression vector. The vector may be used to replicate the nucleic acid in a compatible host cell. It may contain at least one copy (such as multiple copies) of the polynucleotide of the invention. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell. Suitable host cells include bacteria, preferably Gram positive e.g. of the family *Propionibacteriaceae*. Others include *E. coli,* yeast, mammalian cell lines and other eukaryotic cell lines, for example insect cells such as Sf9 cells and (e.g. filamentous) fungal cells.

The polypeptide can be produced as a (secreted) protein in which case the DNA sequence encoding a mature form of the polypeptide in the expression construct is operably linked to a DNA sequence encoding a signal sequence. Preferably the signal sequence is native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast α-factor genes. Similarly, a suitable signal sequence for filamentous fungal host cells is e.g. a signal sequence derived from a filamentous fungal amyloglucosidase (AG) gene, e.g. the *A.niger* glaA gene. This may be used in combination with the amyloglucosidase (also called (gluco)amylase) promoter itself, as well as in combination with other promoters. Hybrid signal sequences may also be used with the context of the present invention.

Suitable heterologous secretion leader sequences are those originating from the fungal amyloglucosidase (AG) gene (glaA—both 18 and 24 amino acid versions e.g. from *Aspergillus*), the α-factor gene (yeasts e.g. *Saccharomyces* and *Kluyveromyces*) or the α-amylase gene (*Bacillus*).

The vectors may be transformed or transfected into a suitable host cell as described above to provide for expression of a polypeptide of the invention or for production of vitamin $B_{12}$. This process may comprise culturing a host cell transformed with an expression vector as described above under conditions to provide for expression by the vector of a coding sequence encoding the polypeptide.

A further aspect of the invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

The invention encompasses processes for the production of the polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is herein defined as a host cell which is of the same species or which is a variant within the same species as the species from which the DNA sequence is derived.

Suitable host cells can be prokaryotic microorganisms such as bacteria, or eukaryotic organisms, for example fungi, such as yeasts or filamentous fungi, or plant cells. In general, yeast cells are preferred over fungal cells because they are easier to manipulate. However, some proteins are either poorly secreted from yeasts, or in some cases are not processed properly (e.g. hyperglycosylation in yeast). In, these instances, a fungal or bacterial host organism can be selected. For production of vitamin $B_{12}$, a prokaryotic or bacterial host is preferred.

The host cell may over-express the polypeptide, and techniques for engineering over-expression are well known[3]. The host may thus have two or more copies of the encoding polynucleotide (and the vector may thus have two or more copies accordingly).

Bacteria from the genus *Bacillus* are suitable heterologous hosts because of their capability to secrete proteins into the culture medium. Other bacteria suitable as hosts are those from the genera *Streptomyces* and *Pseudomonas*. However, preferably the host is from the same order (e.g. Actinomycetales) or family (Propionibacteriaceae) as the bacteria from which the polynucleotides of the invention can be obtained from (*P. freudenreichii*).

A preferred yeast host cell for the expression of the DNA sequence encoding the polypeptide is of the genera *Saccharomyces, Kluyveromyces, Hansenula, Pichia, Yarrowia,* and *Schizosaccharomyces*. More preferably a yeast host cell is selected from the group consisting of the species *Saccharomyces cerevisiae, Kluyveromyces lactis* (also known as *Kluyveromyces marxianus* var. *lactis*), *Hansenula polymorpha, Pichia pastoris, Yarrowia lipolytica,* and *Schizosaccharomyces pombe.*

Most preferred are, however, (e.g. filamentous) fungal host cells. Preferred filamentous fungal host cells are selected from the group consisting of the genera *Aspergillus, Trichoderma, Fusarium, Disporotrichum, Penicillium, Acremonium, Neurospora, Thermoascus, Myceliophtora, Sporotrichum, Thielavia,* and *Talaromyces*. More preferably a filamentous fungal host cell is of the species *Aspergillus oyzae, Aspergillus sojae, Aspergillus nidulans,* or a species from the *Aspergillus niger* Group.[23] These include but are not limited to *Aspergillus niger, Aspergillus awamori, Aspergillus tubingensis, Aspergillus aculeatus, Aspergillus foetidus, Aspergillus nidulans, Aspergillus japonicus, Aspergillus oryzae* and *Aspergillus ficuum,* and further consisting of the species *Trichoderma reesei, Fusarium graminearum, Penicillium chrysogenum, Acremonium alabamense, Neurospora crassa, Myceliophtora thermophilum, Sporotrichum cellulophilum, Disporotrichum dimorphosporum* and *Thielavia terrestris.*

Examples of expression hosts within the scope of the present invention are fungi such as *Aspergillus* species[31,32] and *Trichoderma* species, bacteria such as *Bacillus* species[33,34], e.g. *Bacillus subtilis, Bacillus licheniformis, Bacillus amyloliguefaciens, Pseudomonas* species; and yeasts such as *Kluyveromyces* species[35] e.g. *Kluyveromyces lactis,*[36] and *Saccharomyces* species, e.g. *Saccharomyces cerevisiae.*

Culture of Host Cells and Recombinant Production: [cobA or cbiA]

The invention also includes cells that have been modified to express the polypeptides of the invention. Preferably the host will have at least two, or multiple, copies of the polynucleotide. Such cells include transient, or preferably stable higher eukaryotic cell lines, such as mammalian cells or insect cells, lower eukaryotic cells, such as yeast and (e.g. filamentous) fungal cells or prokaryotic cells such as bacterial cells (e.g of the order Actinomycetales).

It is also possible for the proteins of the invention to be transiently expressed in a cell line or on a membrane, such as for example in a baculovirus expression system. According to the present invention, the production of the polypeptide of the invention can be effected by the culturing of microbial expression hosts, which have been transformed with one or more polynucleotides of the present invention, in a conventional nutrient fermentation medium.

The recombinant host cells according to the invention may be cultured using procedures known in the art. For each combination of a promoter and a host cell, culture condition are available which are conducive to the expression the DNA sequence encoding the polypeptide and/or vitamin $B_{12}$ production. After reaching the desired cell density or titre the culture can be stopped and the polypeptide, or vitamin, is recovered using known procedures.

The fermentation medium can comprise a carbon source (e.g. glucose, maltose, molasses, cellulose, β-glucan etc.) and an (inorganic) nitrogen source (e.g. ammonium sulphate, ammonium nitrate, ammonium chloride, etc.) and/or an (organic) nitrogen source (e.g. yeast extract, malt extract, peptone, etc.). An inorganic nutrient source (e.g. phosphate, magnesium, potassium, zinc, iron, etc.) and/or an inducer (e.g. cellulose, β-glucan, maltose or maltodextrin) may be present.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating micro organisms.

The fermentation can be performed over a period of 0.5-30 days. It may be a batch, continuous or fed-batch process, suitably at a temperature in the range of between 0 and 45° C. and, for example, at a pH between 2 and 10. Preferred fermentation conditions are a temperature in the range of between 20 and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

D. Uses of the Polypeptides in the Biosynthetic Pathway and to Produce Vitamin $B_{12}$ (reaction/Enzyme)

A Amidation ((Amide) Synthase)

An additional aspect of the invention relates to a process of amidation, or for the preparation of an amine, the process comprising contacting a substrate with a polypeptide of the invention. The process therefore includes amidating a substrate. The polypeptide is preferably a synthase, such as an amide synthase. It may be a polypeptide having the sequence of SEQ ID No. 2, or a variant or fragment thereof, as defined earlier, such as in the first aspect. Alternatively, the polypeptide may be a synthase from a bacterium of the family Mycobacteriaceae, for example of the genus *Propionibacterium*, in particular the species *Propionibacterium freudenreichii*.

The process may be conducted in the presence of glutamine. The glutamine may be converted to glutamate in the reaction. The polypeptide may be capable of converting a hydroxyl group into an amine, or a carboxyl group (COOH) into a carboxyamide group ($CONH_2$). The product resulting from the process may therefore be a primary amine.

The process may be repeated, since the polyp eptide may amidate the substrate twice, in other words create two (preferably primary) amine groups on (different) substituents of the substrate. Therefore, the process may involve converting a first carboxyl group to a carboxyamide group. The process may be repeated, and a second. carboxyl group may be converted to a carboxyamide group as well. In this way, this process may involve amidation twice, for example the creation of two separate (e.g. primary) amines. The (second) amidation preferably takes place at a different substituent (e.g. carboxyl group) on the substrate.

Preferably, the substrate is cobyrinid acid or cobyrinic acid c-amide and/or the product is cobyrinic acid c-amide or cobyrinic-a,c-diamide. In this reaction, glutamine can be converted to glutamate. The amount of glutamine added or present may be approximately twice as much as the cobyrinic acid (in other words, glutamine is at a molar concentration of about double the molar concentration of cobyrinic acid). This is because the cobyrinic acid is first amidated to cobyrinic acid c-amide, which acts as an intermediate, and the cobyrinic c-amide is then amidated in a second amidation reaction to give cobyrinic a,c-diamide.

Hence, the polypeptide in this process is preferably a cobyrinic acid a,c-diamide synthase (e.g. cobA or cbiA). The polypeptide may have an activity within EC 6.3.1.-.

B1 (Phospho)transferase (Phosphorylation): [cobU]

The invention also relates to a process of phosharylation, or for the preparation of a phosphate-containing compound, the process comprising contacting a substrate with a polypeptide of the invention. The polypeptide preferably comprises SEQ ID No. 4, or a variant or fragment thereof, as defined earlier. Alternatively, the polypeptide may be a phosphotransferase from a bacterium of the family Mycobacteriaceae, for example of the genus *Propionibacterium*, in particular the species *Propionibacterium freudenreichii*. This process thus comprises phosphorylating (or attaching a phosphate group to) a substrate.

The process may be conducted in the presence of a nucleotidyl (e.g. tri) phosphate, such as ATP. The substrate may comprise a nucleotide, such as one including adenosine.

Preferably the process comprises transfer (from one compound to another, such as to the substrate) of a phosphate moiety, such as phosphorylation of a hydroxyl (OH) group to form a phosphate group ($-PO^-_4$). The polypeptide may thus act as a phosphotransferase with an alcohol group (such as a hydroxy group) as an acceptor.

Preferably the substrate is adenosyl cobinamide (Formula II) and/or the product is adenosyl cobinamide phosphate (Formula IIA). The process may additionally comprise the conversion of a nucleotide triphosphate to a nucleotide diphosphate (for example, ATP to ADP). The polypeptide may therefore be a cobinamide kinase (e.g. cobU). Preferably, it has an activity within EC 2.7.1.-.

B2 (Nucleotidyl)transferase (Nucleotidylation)

In this aspect the invention relates to a process of nucleotidylation, or for the preparation of a nucleotidyl-containing compound, the process comprising contacting a substrate with a polypeptide that is a nucleotide transferase. This polypeptide may be the same as that described in B1 above. This is because the (second) enzyme (designated B), has a dual function, and is a bifunctional enzyme.

Thus enzyme B can act as a general transferase, transferring both phosphate groups as well as nucleotidyl groups. It can therefore act as both a phosphotransferase (B1) and as a nucleotidyl transferase (B2).

The second function, designated B2, relates to the activity of the enzyme as a nucleotidyl-containing transferase.

Thus, preferably the process involved nucleotidylating a substrate, such as guanidylating (a substrate). Preferably, the substrate will comprise at least one phosphate group. Suitably, the polypeptide is able to nucleotidylate a phosphate group.

The process may take place in the presence of a nucleosyl (e.g. tri) phosphate, for example GTP). Thus in this process the polypeptide preferably catalyses the guanidylation of a phosphate group.

Preferably the substrate is adenosyl cobinamide phosphate (Formula IIA) and/or the product is adenosyl-GDP-cobinamide (Formula IIB). Thus the enzyme can catalyse the formation of a nucleotidyl-containing compound, such as adenosyl-GDP-cobinamide, from a substrate such as adenosyl cobinamide phosphate. The polypeptide may thus be a (nucleotidyl) transferase, or has an activity within EC 2.7.7.-. Other preferred features of the polypeptide are as described in the previous section concerning phosphotransferase activity (B1).

C Arylation (Aryl Transferase) or Ribazole Addition: [cobS]

This process of the invention comprises arylation, or the preparation of an aryl-containing compound, the process comprising contacting a substrate with a polypeptide of the invention, preferably an (e.g. aryl) transferase. Preferably the polypeptide comprises SEQ ID No. 6, or a variant or fragment thereof as previously defined. Alternatively, the polypeptide may be an aryltransferase from a bacterium of the family Mycobacteriaceae, for example of the genus *Propionibacterium*, in particular the species *Propionibacterium freudenreichii*. This process thus comprises arylating a substrate.

The aryl moiety (e.g. in ribazole, such as is transferred during a reaction) may comprises an aromatic ring system. The aryl moiety may comprise one or two aromatic rings. The ring system may be substituted by from one to four $C_{1-8}$ alkyl groups. The aryl moiety may comprise none, one or two heteroatoms, for example one or two nitrogen atoms. Preferably the aryl moiety comprises a benzimidazole ring. The process therefore may comprise the preparation of a (e.g. dimethyl) benzimidazole (DMB)-containing compound.

The aryl group may be bonded or joined to a (central) metal, e.g. cobalt, atom. Alternatively or in addition, the aryl group may be bonded to a carbon atom, such as in a ribose group. Preferably the aryl moiety is bonded to both cobalt atom and a ribose group (in the product of the reaction, namely the resulting benzimidazole-containing compound).

The process may take place in the presence of a ribazole, such as α-ribazole. This may be present in an approximately equimolar amount to the substrate. The reaction may comprise alpha-ribazole addition (to the substrate).

Preferably the substrate is adenosyl-GDP-cobamide. The product of the reaction, the aryl-containing compound, is preferably adenosyl-5,6-dimethyl benzimidazolyl cobamide (Formula IIC). In. the process of the reaction, the ribazole may be converted to GMP.

Preferably the polypeptide used in this process is a cobalamin (5'-phosphate) synthase (e.g. cobS). The polypeptide may have the activity EC 2.7.8.-.

D Adenosylation (Adenosyl Transferase)

This process of the invention relates to adenosylation, or the preparation of an adenosine-containing compound, the process comprising contacting a substrate with a polypeptide of the invention, preferably a transferase, such as an adenosyl transferase. The polypeptide preferably comprises SEQ ID No. 7, of fragment or variant thereof, as previously defined. Alternatively, the polypeptide may be a transferase from a bacterium of the family Mycobacteriaceae, for example of the genus *Propionibacterium*, in particular the species *Propionibacterium freudenreichii*. This process thus comprises adenosylating a substrate.

This process may therefore comprise the transfer of adenosine, preferably to the substrate. Preferably the adenosine becomes bound to a metal atom, such as a transition metal (such as of the first series), for example cobalt.

The substrate (and/or product) may be an amide, such as a diamide. Preferably the substrate is cobyrinic acid a, c diamide and/or the product is adenosyl cobyrinic acid a, c diamide.

The process may take place in the presence of a nucleosyl (e.g. tri) phosphate, such as ATP. It may also take place in the presence of adenosine. Preferably, both the adenosine and the nucleosyl phosphate are present in approximately equimolar amounts to the substrate. The nucleosyl triphosphate may be converted to a nucleosyl diphosphate.

Preferably the polypeptide in this process is an adenosyl transferase. It may have an activity within EC 2.5.1.7. Preferably, the polypeptide is a transferase that is capable of transferring alkyl or aryl groups, other than methyl groups. Polypeptides that methylate, or cause methylation, may thus be excluded.

Substrates (or Products of Catalysed Reaction): Vitamin $B_{12}$ Intermediates and/or Precursors The substrate and/or product preferably comprises a corrin core or ring system. Preferably, it comprises an aryl ring system, with up to four rings (which may be the same or different). Preferably however there are four rings, and they are the same. Each ring may contain one or two heteroatoms, for example one nitrogen atom. The ring may be pentagonal. Thus preferred rings are pyrrole, and therefore the ring system preferably comprises a tetrapyrrole system. Preferably two of the pyrrole rings are joined to each other, and the other two pyrrole rings are joined by a bridge, such as by methene units.

The ring system may comprise a metal atom, for example at its core. This metal may be a transition metal, for example of the first series (group VIII). It may be of period four. Preferably the metal is cobalt, and this may be a single central cobalt atom. The ring system may have attached to it an amide, phosphate, guanidyl or adenosyl moiety or group. In addition to the metal atom and ring system, there may be a fifth, and optionally even a sixth substituent, for example bound to the metal. The or each substitutuent may be above and/or below the plane of the ring, as applicable. Where appropriate (and in the case of vitamin $B_{12}$), one of these substituents may comprise a nucleosyl group, such as a dioxy nucleosyl, preferably 5'-dioxy adenosine. Another substituent may be an aryl group as defined above in section C concerning arylation. This substituent may therefore preferably comprise dimethoxybenzimidazole. In substrates employed in the invention, one or both substituents may be present, and so that the cobalt atom may have, as fifth and sixth substituents, a 5'-dioxy adenosine and a dimethoxy benzimidazole group. The same preferred features apply to the product of the reaction as they do to the substrate.

A list of the substrates and products of the five catalysed reactions, or biosynthetic steps, is provided below after the role of the enzymes in the vitamin $B_{12}$ biosynthetic pathway.

| Formula Enzyme | A (cobA) Uro III ⟶ ⟶ ⟶ ⟶ Cobinamide Common name | B (cobU) ⟶ cobinamide-P Reaction/Biosynthetic step: | C (cobS) ⟶ Vitamin B$_{12}$ |
|---|---|---|---|
| I | cobyrinic acid ↓ | A | amide synthase |
| IA | cobyrinic acid c-amide ↓ | A | amide synthase |
| IB | cobyrinic acid a,c-diamide ↓ | D | (adenosyl) transferase |
| IC | adenosyl cobyrinic acid-a,c-diamide | | |
| II | adenosyl cobinamide ↓ | B1 | (phospho) transferase |
| (cobU) IIA | adenosyl cobinamide phosphate ↓ | B2 | (nucleotidyl) transferase |
| (cobU) IIB | adenosyl-GDP cobamide ↓ | C | (benzimidazolyl) |
| transferase (cobS) IIC | adenosyl-5,6 dimethyl benzimidazolyl cobamide (vitamin B$_{12}$) | | |

Preferred intermediates or precursors include cobinamide, cobinamide-P (phosphate) or compounds of Formula 1A, 1B, II, IIA, IIB or IIC.

Hence the process of the present invention may comprise one or more of the following process steps (illustrated using chemical formulae), namely:

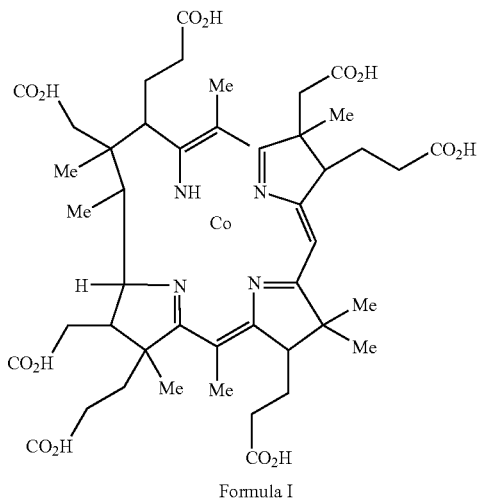

Formula I

↓ (amide) synthase (A)
(SEQ ID No. 2, or variants, etc thereof)

-continued

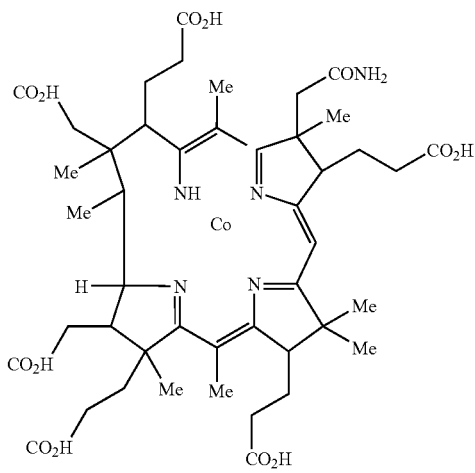

Formula IA

↓ (amide) synthase (A)
(SEQ ID No. 2, or variants, etc thereof)

-continued
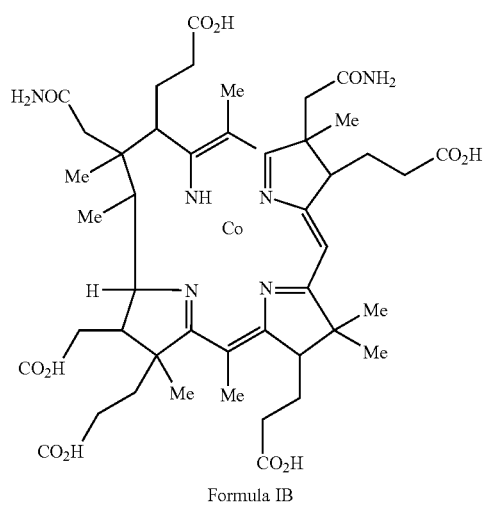
Formula IB
↓ adenosyl transferase (D)
(SEQ ID No. 8, variants, etc thereof)
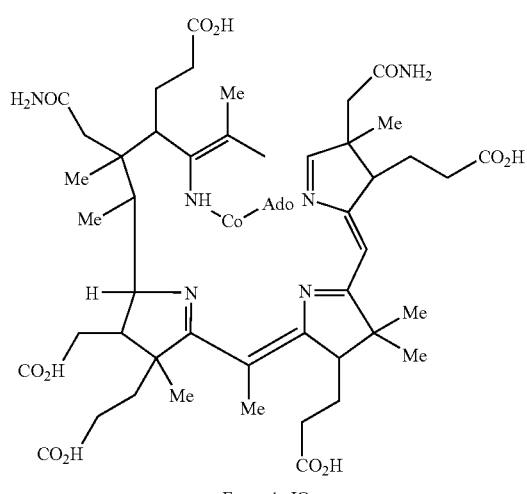
Formula IC
-continued
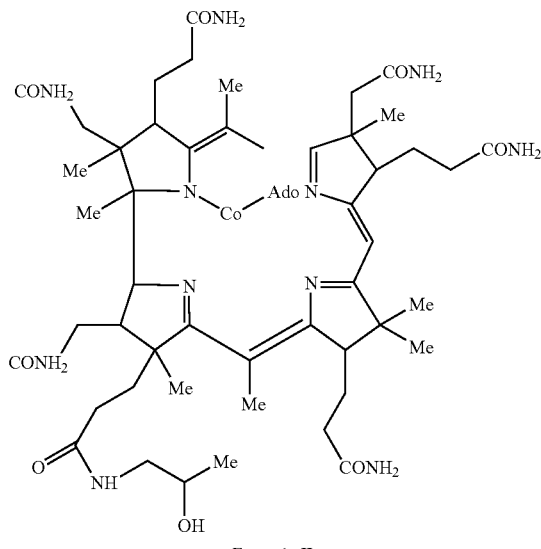
Formula II
↓ (phospho) transferase (B1)
(SEQ ID No. 4, or variants, etc. thereof
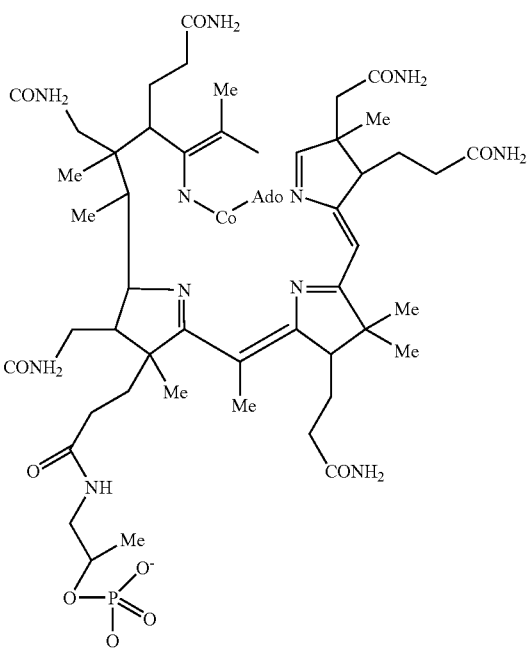
Formula IIA
↓ (nucleotidyl) transferase (B2)
(SEQ ID No. 4, or variants, etc. thereof)

-continued

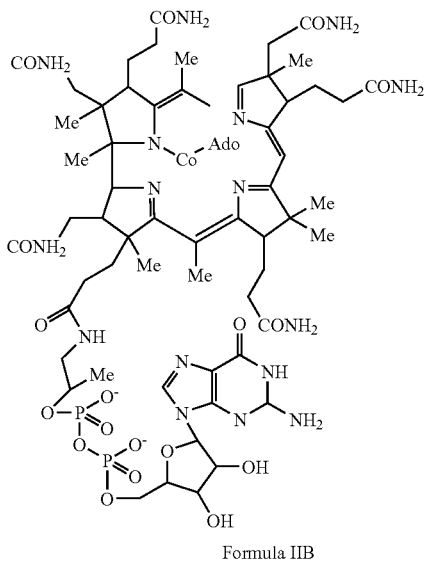

Formula IIB

↓ (benzimidazolyl) transferase (C)
(SEQ ID No. 6, or variants, etc. thereof

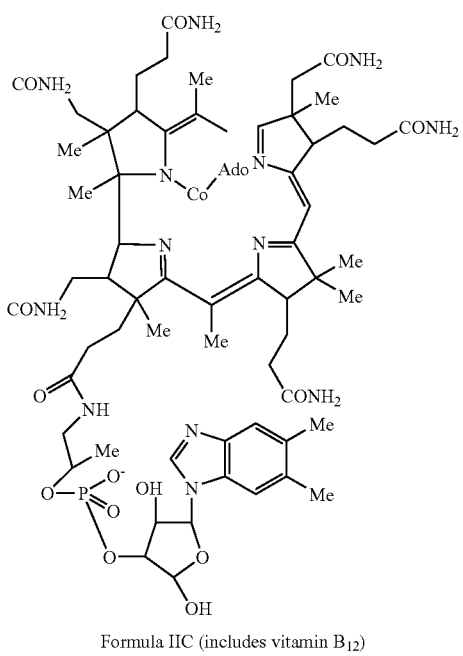

Formula IIC (includes vitamin $B_{12}$)

E. Industrial Preparation of Vitamin $B_{12}$

As described above, the polypeptides of the invention may be used to perform one or more biosynthetic steps in the vitamin $B_{12}$ preparatory pathway. The polypeptide may be contacted with the appropriate substrate and the reaction allowed to take place. This may be allowed to occur when the polypeptide is outside a (e.g. host) cell, in other words the polypeptide is mixed with the substrate, for example in vitro. However, it is considerably more effective to use a host cell of the invention, comprising one or more of the polypeptides of the invention, in order to either perform one or moreparticularly desired steps in the vitamin $B_{12}$ biosynthetic pathway or, preferably, use the host cell to produce vitamin $B_{12}$ (or an intermediate or precursor thereof).

The invention therefore also relates to a process for preparing vitamin $B_{12}$ (or a precursor thereof), the process comprising culturing one or more host cells of the invention under conditions that allow the cells to biosynthesise (and hence produce) vitamin $B_{12}$ (or the precursor).

This process may take place in a fermenter. The fermenter may be equipped with agitation means, for example a stirrer. The fermenter vessel may also be equipped with aeration means, such as a means of causing an oxygen-containing gas to be contacted with a liquid in the fermenter. The liquid will usually be the culture broth, consisting of an aqueous suspension of the cells. Fermentation may then be allowed to take place. The fermenter may have a minimum volume of 10, 50, 100 or 1,000 litres.

The cells may be supplied with one or more carbon and/or nitrogen sources, before fermentation begins, at the start of fermentation, or continuously or continually during fermentation.

At the end of the fermentation, the supply of the carbon or nitrogen sources is stopped, or one or more of these sources may be used up. Each of the carbon and/or nitrogen sources may be a complex source or an organic or inorganic compound.

The cells may then be removed from the fermenter. Before or after this, water (or an aqueous liquid) may be removed from the cells. The cells may then be heated or pasteurised, in order to kill them.

Methods of extracting or isolating vitamin $B_{12}$ from microbial cells are well known[45]. For example (in order to be able to obtain the vitamin B12) it is preferred that the host cells, having produced the vitamin, are broken, or at least partially opened, so that at least part of the soluble content of the cells (comprising vitamin B12) is released into a liquid, for example a liquid in which the cells are contained. One can then separate the open or broken cells, or resulting cell debris, from the liquid (comprising the vitamin B12). The microbial cells (containing vitamin B12) can thus be treated so as to cause disruption of the cell membranes. Suitable treatments for opening the cells include heat treatment, such as pasteurisation, heating in an autoclave, treatment with bacteriolytic enzymes (such as lysozyme), and/or mechanical disruption cells (grinding, or the use of shear forces), or treatment of chemicals (to cause cell lysis, for example the use of detergents or organic solvents).

The process of lysis or other membrane disruption can produce a lysate, which can then be separated into solid and liquid phases. The solid phase of the lysate, comprising the cell debris, can then be separated (from the liquid containing vitamin B12). A number of suitable solid-liquid separation techniques are available, including centrifugation and/or filtration. Preferably however, solid liquid separation is performed using ultrafiltration.

Preferably, the open/broken microbial cells are washed, and the washings are then combined or added to the (vitamin B12 containing) liquid, separated from cell debris. Suitably washing comprises diafiltration,suitably with ion-free water. The (vitamin B12) containing diafiltrate can then be combined with the (vitamin B12 containing) liquid phase.

The vitamin B12 containing liquid(s) may then be subjected to drying, for example spray-drying, fluid-bed drying, freeze drying or drying in a vacuum.

Preferably, cells producing vitamin B12 are washed prior to opening (lysis), since this may increase the vitamin B12 concentration on dry matter by removing medium components. This can be performed using diafiltration, preferably using ion-free water.

Preferred features and characteristics of one aspect of the invention are applicable to another aspect mutatis mutandis.

The invention will now be described with reference to the following Examples which are intended to be illustrative only and not limiting.

EXAMPLE 1

Propionibacterium Vectors

Two strains (P. freudenreichii LMG1 6545 and P. freudenreichii LMG16546) were used which both show an identical plasmid profile of 2 plasmids. One plasmid was large (size not determined) and the other was smaller, more abundantly present and had a size of 3.6 kb. These 3.6 kb plasmids from LMG16545 and LMG16546 were chosen for further use in vectors. Plasmids from these vectors already are described.[29] Expression systems in Propionibacteria are known in the art[30].

Construction of E. coli/Propionibacterium Shuttle Vectors

A 1.7 kb Acc65I fragment from the Saccharopolyspora erythraea NRRL2338 erythromycin biosynthesis cluster and containing the erythromycin resistance conferring gene[37,38] was inserted into Acc65I linearized pBR322ΔI[29]. Then the newly derived construct, named pBRES, was linearized with EcoRV and ligated to p545 DNA that had been digested with BsaBI. E.coli transformants were found to harbor a vector with the correct insert, in both orientations. The resulting plasmid vectors were named pBRESP36B1 and pBRESP36B2 (see FIGS. 2a and 2b[29]).

Plasmid vector constructs were also obtained with p545 DNA linearized in an other restriction site situated outside the putative replication region, namely AlwNI. For this construction the pBRES vector had to be provided with a suitable cloning site. An adaptor was designed and annealing of the required oligo's created a double stranded DNA fragment with Acc65I and BglII cohesive ends respectively, which moreover contains an internal SfiI restriction site, that provides ends compatible to the AlwNI digested p545 plasmid. This adaptor was cloned in pBRES between the BglII and the proximal Acc65I site. The pBRES-Sfi vector thus obtained was subsequently digested by SfiI and ligated to AlwNI digested p545. Transformation of E.coli yielded transformants with the correct vector as confirmed by restriction enzyme analysis. The vector obtained was named pBRESP36A[29].

Transformation of Propionibacterium with E. coli/Propionibacterium Shuttle Vectors Transformation of Propionibacterium freudenreichii strain ATCC6207 with pBRESP36B1 will be described.

The bacterial cells are cultivated in SLB (sodium lactate broth[39] at 30° C. to a stationary growth phase, and subsequently diluted 1:50 in fresh SLB. After incubation at 30° C. for around 20 hours, cells (now in the exponential growth phase) were harvested and washed extensively in cold 0.5M sucrose. Subsequently cells were washed once in the electroporation buffer, consisting of 0.5M sucrose, buffered by 1mM potassium acetate, pH5.5, and finally resuspended in this electroporation buffer in about 1/100 of the original culture volume. Cells were kept on ice during the whole procedure.

For the electroporation (apparatus from BIORAD), 80-100 μl of cell suspension was mixed with ±1 μg of DNA (or smaller amounts), in a cooled 1 or 2 mm electroporation cuvette, and an electric pulse delivered. Optimal pulse conditions were found to be 25 kV/cm at 200 Ω resistance and 25 μF capacitance. However, lower and higher voltages (also at 100 Ω) also yield transformants.

Immediately after the pulse, 900 μl cold SLB containing 0.5 M sucrose was added to the pulsed cell suspension and these are subsequently incubated for 2.5 to 3 hours at 30° C. before plating appropriate dilutions on SLB/agar plates containing 0.5 M sucrose and 10 μg/ml erythromycin. After a 5 to 7 day incubation period at 30° C. under anaerobic conditions, transformants were detected.

DNA isolated from E. coli DH5α (Promega) yielded a transformation efficiency of 20-30 transformants per μg DNA. A 10-100 fold higher efficiency is achieved when DNA is isolated from E. coli JM110 (dam$^-$, dcm$^-$ strain). E. coli transformation was done according to BIORAD's instructions.

Transformants contained the authentic vectors, indistinguishable from the original plasmid DNA used for transformation of ATCC6207. This was shown by restriction enzyme analysis of plasmid DNA isolated from the transformants by the small scale plasmid DNA isolation procedure refered to before.

Vectors were exclusively present as autonomously replicating plasmids. Southern blot hybridizations with total DNA isolates showed that chromosomal DNA did not hybridise to the vector DNA used as a probe, indicating that no chromosomal integration of plasmid DNA occured.

Transformation was also successful with vectors pBRESP36B2 and pBRESP36A, indicating that functionality of the vector was independent of the orientation of p545 or the cloning site used. Also in this case the authenticity of the vectors was confirmed.

Moreover, transformation of P. freudenreichii strain ATCC6207 with DNA isolated from a Propionibacterium transformant resulted in a $10^5$-$10^6$ fold increased transformation efficiency as compared to that obtained with DNA isolated from E. coli DH5α.

Transformation of another P.freudenreichii strain, LMG16545 (the same strain from which the p545 plasmid was obtained), resulted in a transformation efficiency comparable to that of the ATCC strain.

The transformations we repeated using each of SEQ ID Nos. 1, 3, 5 and 7 operably linked to appropriate transcription and translation start signals in the shuttle vector.

EXAMPLE 2

Construction of Plasmid Vector Containing the Amide Synthase (A) Gene

The construction and application of a plasmid vector to increase the level of vitamin $B_{12}$ (cobalamine) synthesis in P. freudenreichii strain ATCC6207 will be described.

For construction of gene overexpression plasmids use was made of the 16S rRNA promoter from P. freudenreichii. One of the strategies to test promoter bearing fragments is the use of a promoter-probe vector. The reporter gene used to monitor promoter activity encodes an easily detectable enymatic activity that is not present in the wild type strain. The cat (chloramphenicol acetyl transferase) gene from pACYC184[17,42] was used for construction of a promoter-probe vector. In order to analyse the activity of the 16S rRNA promoter this promoter was placed upstream of the cat gene.

For construction of the promoter-probe vector, the promoterless cat gene was cloned in the *E. coli/Propionibacterium* shuttle vector pBRESP36B2[29] by PCR, resulting in vector pB2/PoCAT. The upstream PCR primer included the sequence 5'-GGGATCCTCTAGAGCATGCAAGCTTCTC-GAGAATCGATAGATCTCTAAGGAAGCT AAAATG-3' (SEQ ID No.9), in which the last three nucleotides indicate the start codon of the cat gene. This synthetically derived sequence includes a multi-cloning site (MCS) containing the restriction sites BamHI, XbaI, HindIII, SphI, XhoI, ClaI and BglII. The downstream PCR primer included a BamHI restriction site. After PCR amplification the cat gene was cloned as a BamHI fragment in the BglII site of the vector (BamHI and BglII sites not restored). Two orientations of the cat gene were obtained. The orientation in which the cat gene has the same orientation as the beta lactamase gene in the pBR322 segment was used in further experiments.

On the basis of the sequence of 16S rRNA from *Propionibacterium freudenreichii* ATCC6207 (GenBank accession number X53217) an appropriate restriction enzyme was chosen (HindIII) and appropriate PCR primers were designed that enabled the amplification of an approximately 3 kb region encompassing the promoter by inverse PCR[2]. From the PCR fragment a 0.6 kb SphI-HindIII fragment directly upstream of the 16S rRNA coding sequence was isolated. This fragment was ligated in pB2/PoCAT digested with the same enzymes resulting in a plasmid named pB2/PrRNA-CAT. After transformation of *E. coli* chloramphenicol resistant transformants were obtained. After transformation *P. freudenreichii* strain ATCC 6207 colonies were only obtained on erythromycin containing plates, not on chloramphenicol containing plates. However, when streaked on chloramphenicol containing plates transformants containing pB2/PrRNA-CAT grew whereas ATCC6207 cells containing pB2/PoCAT did not grow, thus indicating the functionality of the 16S rRNA in *P. freudenreichii*.

An expression vector containing the 16S rRNA promoter but lacking the cat gene was constructed by ligation of the approx. 700 bp BamHI-BglII fragment from vector pB2/PrRNACAT, containing the 16S ribosomal RNA promoter from *P. freudenreichii*, into the unique BglII of pBRESP36B2. Both possible orientations of the promoter element in the vector were obtained. In case transcription of genes expressed by this ribosomal promoter was not properly terminated, readthrough may obstruct transcription of the two replication genes of the *Propionibacterium* replicon if the ribosomal promoter is oriented towards these replication genes. Therefore the vector in which the promoter was cloned in the opposite orientation, pBRESP36B2p16SH, was used in further experiments. A unique BglII site downstream from the promoter was used for cloning of the expression library.

EXAMPLE 3

The complete coding sequence of adenosyl transferase (D, SEQ ID No. 7) was generated by PCR from appropriate primers. The upstream PCR primer included a 5' extension including a BglII restriction site and a ribosome binding site upstream of the start codon of the gene. The downstream PCR primer included a 5' extension including a BglII restriction site. After digestion of the amplified fragment with BglII the fragment was ligated in the vector pBRESP36B2p16SH and digested with BglII and dephosphorylated to remove 5' phosphate groups. After transformation of *E. coli* ampicillin resistant colonies were obtained. Both orientations of the cloned fragment releative to the vector were observed. However, only the construct in which the 16S rRNA promoter is located directly upstream of the ribosome binding site allows the expression of the adenosyl transferase gene.

The latter construct was transformed to *P. freudenreichii* ATCC6207 as described before. In the transformants the level of vitamin $B_{12}$ synthesis was determined as follows. Frozen cultures of *Propionibacterium* transformants, as well as a control strain containing only the vector plasmid pBRESP36B2, were inoculated in 100 ml flasks containing 50 ml of BHI (Brain Heart Infusion) medium (Difco) and incubated for 72 hrs at 28° C. without shaking. From this preculture 4 ml were transferred to 200 ml of production medium consisting of Difco yeast extract 15 g/l, Na lactate 30 g/l, $KH_2PO_4$ 0.5 g/l, $MnSO_4$ 0.01 g/l, and $CoCl_2$ 0.005 g/l in a 500 ml shake flask and incubated at 28° C. for 56 hrs without shaking, followed by 48 hrs in a New Brunswick rotary shaker at 200 rpm.

Vitamin $B_{12}$ titres were measured using HPLC[43] and showed a higher vitamin $B_{12}$ production than the control strain.

The process was repeated for each of the other three genes namely:

A: SEQ ID No. 1, cobyrinic acid-a, c-diamide synthase;
B: SEQ ID No. 3, cobinamide kinase gene; and
C: SEQ ID No. 5, cobalamin (5'-phosphate) synthase.

The four genes (A, B, C, and D) were then combined in one operon to further increase vitamin $B_{12}$ production.

The resulting transformed cells (the *P. freudenreichii*) ATCC 6207) was cultured in a fermenter using a known technique[44]. In order to kill the cells, and to cause lysis, the broth was pasteurised at 65° C. for thirty minutes. The broth was then subjected to ultrafiltration, and a pink coloured filtrate was obtained, containing vitamin $B_{12}$. The heat had caused lysis of the cells, and therefore release of the intracellular vitamin $B_{12}$ in the medium.

EXAMPLE 4

Construction of Expression Vectors for *Propionibacteria* and Its Use in Expression of Enzymes of the Invention and Production of Vitamin $B_{12}$ in *Propionibacterium freudenreichii*

Apart from the expression systems described above[29,30], two other expression systems are known in the art that can be used to express, in multiple copies if desired, genes encoding the novel enzymes of the invention. The first is pRG01, a plasmid from *Proprionibacterium acidipropionici*[27]. This was used to create a shuffle vector pPK705. Such a vector was used to carry successfully the cobyrinic acid a,c-diamide synthase (A) enzyme, and thus transform *Propionibacterium freudenreichii* subspecies *shermanii*.

The other suitable expression system that was employed used the known shuttle vector pPK705[28], which is able to shuttle between *E. coli* and *Proprionibacterium*. This allowed the construction of expression vectors for *Proprionibacteria*, and the incorporation of enzyme B, cobinamide kinase, into *Freudenreichii* subspecies *shermanaii*. This was achieved by using the cobinamide kinase gene, SEQ ID No. 3 of the invention.

COMPARATIVE EXAMPLE 5

Shake Flask Fermentation of *Propionibacterium* Containing an Empty Plasmid Vector The transformation of *P. freudenreichii* strain ATCC6207 with the *E. coli/Propionibacterium* shuttle vector pBRESP36B2p16SH has been described in Example 2. Transformants were selected on erythromycin containing agar plates as described before and transformants containing the authentic plasmid were selected by restriction analysis.

Transformants were grown in brown-glass penicillin flasks containing 50 ml of anaerobic M1 culture medium prepared as follows. 900 grams of M1 culture medium was prepared by adding 90 ml of part B to 810 grams of part A under anaerobic conditions. Erythromycin was added to a final concentration of 10 milligram/liter.

810 grams of part A consisted of 52.2 g MES, 12.51 g Difco Yeast Extract and 0.68 g methionine dissolved in water. The pH was adjusted to 7 with ammonium hydroxide and the oxygen was removed by degassing and flushing with nitrogen. Finally part A was sterilized in an autoclave.

90 ml of part B consisted of 1.5 ml trace element solution, 1.5 ml filter sterilized CoCl2.6H2O (5 g/kg), 0.9 ml filter sterilized Ca-pantothenate (20 g/kg) and 86.1 ml degassed sterile glucose (440 g/kg).

1 kg of trace elements solution contained 10 g citric acid, 10 ml H2SO4, 1.2 g MnSO4.H2O, 300 g MgSO4.7H2O, 6 g FeSO4.7H2O and 2.4 g ZnSO4.7H2O in water. The solution was filter sterilized.

The 50 ml M1 medium was inoculated under anaerobic conditions with 5 ml of an pre-culture that consisted of a selected pBRESP36B2p16SH transformant that had been grown anaerobically in M1 culture medium for 3 days at 30° C. with gentle shaking until an OD630 of approximately 10.

The 50 ml culture was incubated for 40 hours at 30° C. without shaking. At this time-point a sample was taken from the culture and the OD630 determined (=OD-ana); The pH of the medium was corrected through the anaerobic addition of NaOH (10%). The number of microliters of NaOH (10%) needed were calculated using the formula: number of microlitres NaOH (10%)=(19.67×OD-ana)−60. As a next step 0.5 ml of DBI (0.5 g/kg) was anaerobically added. Following these additions the culture was incubated for another 24 hrs at 30° C. with shaking at 200 rpm. The OD630 was determined again (=OD-end).

10 ml samples of the cultures were collected. The cells were harvested by centrifugation and the pellet was washed once with 1 volume sterile demineralised water. The pellet was stored at −20° C. Thawed samples were heated to 80° C. in a 2% KCN containing buffer to open the cells and to stabilise vitamin B12 and precursors. Vitamin B12 titers as well as adenosyl cobinamide and adenosyl cobinamide phosphate precursor levels were measured using HPLC using appropriate standards (43). The identity of the adenosyl cobinamide and adenosyl cobinamide phosphate precursor peaks was established on the basis of mass spectrometry data.

The amount of vitamin B 12 produced per ml culture of pBRESP36B2p16SH transformants was divided by OD-end. The resulting ratio obtained for pBRESP36B2p16SH transformants was used as a reference for the ratios obtained for *P. freudenreichii* transformants containing other plasmids (e.g. next example). Similar ratios were calculated for the amounts of adenosyl cobinamide and adenosyl cobinamide phosphate produced (amount per ml culture per OD-end). These ratios were used as reference for the ratios obtained for respectively adenosyl cobinamide and adenosyl cobinamide phosphate in *P. freudenreichii* transformants containing other plasmids.

EXAMPLE 6

Construction of an Expression Vector for the *Propionibacterium freudenreichii* cobA/cbiA Gene and Its Use for the Production of Vitamin B12 and Its Precursors in *Propionibacterium freudenreichii*

A *Propionibacterium freudenreichii* gene coding for glutamate 1-semialdehyde aminomutase named hemL[46] (EMBL accession number D12643) was used. The coding region of this gene is followed by the transcriptional hemL terminator. A DNA fragment containing the coding region of the hemL gene and the hemL terminator was cloned in pBRESP36B2p16SH as described in the following steps. The DNA fragment was amplified by PCR from chromosomal DNA isolated from *P. freudenreichii* ATCC6207 using the following primers: 5'-CAgTAgATCT CgACAAggAggAAC-CAtgAg-3'(SEQ ID No.10) and 5'-CgTAAgATCT-CAgTTTCggACATggCAgTg-3'(SEQ ID No.11). Both primers contain a BglII restriction site. The PCR fragment obtained was ligated into the vector pCR-Blunt II-TOPO (Invitrogen) to create pGBPHEL-1. After transformation of *E. coli* kanamycin resistant colonies were obtained. The constructs thus obtained were verified by restriction analysis and the DNA sequence of the fragment was verified through sequence analysis.

pGBPHEL-1 was subsequently digested with BglII and the fragment containing the hemL gene was isolated and ligated into the vector pBRESP36B2p16SH which first had been digested with BglII and dephosphorylated. After transformation of *E. coli* ampicillin resistant colonies were obtained. A construct in which the hemL gene is transcribed from the 16S promoter was selected by restriction analysis. The resulting construct was called pGBP01HEL-1.

A *P. freudenreichii* gene coding for uroporphyrinogen III methyltransferase named cobA (EMBL accession number U13043) was used[47]. In order to over-express the cobA gene in *Propionibacterium* the gene was placed behind the 16S rRNA promoter and in front of the hemL terminator present in pGBP01HEL-1 as described in the following steps. A DNA fragment containing the cobA coding region was amplified by PCR from chromosomal DNA isolated from *P. freudenreichii* ATCC6207 using the following primers: 5'-CACCACCAA-CATCgATgAggAAAC-3'(SEQ ID No.12) and 5'-TCCAAT-TgggACTCAgTggTCgCTg-3'(SEQ ID No.13). The first primer contains a ClaI and the second primer contains a MfeI restriction site. The PCR fragment obtained was ligated into the vector pCR-Blunt II-TOPO (Invitrogen). After transformation of *E. coli* kanamycin resistant colonies were obtained. The DNA sequence of the cloned fragment was verified through sequence analysis. The resulting construct was named pGBPCOB-1.

pGBPCOB-1 was subsequently digested with ClaI and MfeI and the fragment containing the cobA gene was isolated and ligated into the large vector fragment isolated from pGBP01HEL-1 digested with the same enzymes. After transformation of *E. coli* ampicillin resistant colonies were obtained. Plasmid DNA isolated from transformants was verified by restriction analysis and the resulting construct was called pGBP02COB-1.

pGBP02COB-1 was transformed to *E. coli* JM101 and plasmid DNA isolated from the obtained transformants was verified by restriction analysis. The plasmid DNA was subsequently transformed to *P. freudenreichii* ATCC6207 as described before. Transformants were selected on erythromycin containing agar plates as described before. The plasmid DNA isolated from the *P. freudenreichii* transformants was verified by restriction analysis.

Shake flask fermentations of pGBP02COB-1 transformants using M1 culture medium and the determination of vitamin B12, adenosyl cobinamide and adenosyl cobinamide phosphate levels were performed as described in the previous Example.

Ratios of the amount of vitB12, adenosyl cobinamide and adenosyl cobinamide phosphate produced per ml culture OD-end were calculated as described in the previous example. The ratio obtained for vitB12 was 6% lower than that obtained for pBRESP36B2p16SH transformants in the previous example. However, the ratio obtained for adenosyl cobinamide was 227% higher than that obtained for pBRESP36B2p16SH transformants and the ratio obtained for adenosyl cobinamide phosphate was 200% higher than that obtained for pBRESP36B2p16SH transformants. Thus there was a 2-fold increase in cobinamide and 3-fold increase in cobinamide P over the empty plasmid (Comparative Example 5).

EXAMPLE 7

Construction of an Expression Vector for the *Propionibacterium freudenreichii* Gene Encoding Protein B (cob U) and Its Use For the Production of Vitamin B12 and Its Precursors in *Propionibacterium freudenreichii*

In order to over-express the gene coding enzyme B (SEQ ID No.3) in *Propionibacterium* the gene was placed behind the 16S rRiNA promoter and in front of the hemL terminator present in pGBPO1HEL-1 as described in the following steps. A DNA fragment containing the coding region for B was amplified by PCR from chromosomal DNA isolated from *P. freudenreichii* ATCC6207 using the following primers: 5'-CTgATATCAATTggAggACATCAgAT-gACCCgCATCgTC-3'(SEQ ID No.14) and 5'-CTgAATTCg-gCCACgTCAgATCgCgTCC-3'(SEQ ID No.15). The first primer contains an EcoRV and a MfeI restriction site and the second primer contains an EcoRI restriction site. The PCR fragment obtained was ligated into the vector pCR-Blunt II-TOPO (Invitrogen). After transformation of *E. coli* kanamycin resistant colonies were obtained. The DNA sequence of the cloned fragment was verified through sequence analysis. The resulting construct was named pGBPCOU-1.

pGBPCOU-1 was subsequently digested with EcoRV and EcoRI and the fragment containing the gene coding for B was isolated and ligated into the large vector fragment isolated from pGBP01HEL-1 which was first digested with ClaI, than blunted with Klenow enzyme, and finally digested with MfeI. After transformation of *E. coli* ampicillin resistant colonies were obtained. Plasmid DNA isolated from transformants was verified by restriction analysis and the resulting construct was called pGBP02COU-1.

pGBP02COU-1 was transformed to *E. coli* JM101 and plasmid DNA isolated from the obtained transformants was verified by restriction analysis. The plasmid DNA was subsequently transformed to *P. freudenreichii* ATCC6207 as described before. Transformants were selected on erythromycin containing agar plates as described before. The plasmid DNA isolated from the *P. freudenreichii* transformants was verified by restriction analysis.

Shake flask fermentations of pGBP02COU-1 transformants using M1 culture medium and the determination of vitamin B12, adenosyl cobinamide and adenosyl cobinamide phosphate levels were performed as described before.

Ratios of the amount of vitaminB12, adenosyl cobinamide and adenosyl cobinamide phosphate produced per ml culture OD-end were calculated as described before. The ratio obtained for adenosyl cobinamide was 96% lower than that obtained for pBRESP36B2p16SH transformants and the ratio obtained for adenosyl cobinamide phosphate was 700% higher than that obtained for pBPESP36B2p16SH transformants. Thus there was a 7-fold increase in the intermediate cobinamide-P when compared with the empty plasmid.

EXAMPLE 8

Construction of an Expression Vector for the *Propionibacterium freudenreichii* Genes Encoding Protein B and C (cob U and S) and Its Use For the Production of Vitamin B12 and Its Precursors in *Propionibacterium freudenreichii*

In order to over-express simultaneously the genes encoding enzymes B (SEQ ID No.3) and C (SEQ ID No.5) in *Propionibacterium* the genes were placed behind the 16S rRNA promoter and in front of the hemL terminator present in pGBP01HEL-1 as described in the following steps. The two genes are located next to each other on the *P. freudenreichii* genome and are part from the same operon. A DNA fragment containing both genes was amplified by PCR from chromosomal DNA isolated from *P. freudenreichii* ATCC6207 using the following primers: 5'- CTgATATCAATTggAggACAT-CAgATgACCCgCATCgTC-3'(SEQ ID No.16) and 5'-CT-gAATTCCggCggCTCAggCgAACAATg-3'(SEQ ID No.17). The first primer contains an EcoRV and a MfeI restriction site and the second primer contains an EcoRI restriction site. The PCR fragment obtained was ligated into the vector pCR-Blunt II-TOPO (Invitrogen). After transformation of *E. coli* kanamycin resistant colonies were obtained. The DNA sequence of the cloned fragment was verified through sequence analysis. The resulting construct was named pGBPPOB-1.

pGBPPOB-1 was subsequently digested with EcoRV and EcoRI and the fragment containing the genes coding for B and C was isolated and ligated into the large vector fragment isolated from pGBP01HEL-1 which was first digested with ClaI, than blunted with Klenow enzyme, and finally digested with MfeI. After transformation of *E. coli* ampicillin resistant colonies were obtained. Plasmid DNA isolated from transformants was verified by restriction analysis and the resulting construct was called pGBP02POB-1.

pGBP02POB-1 was transformed to *E. coli* JM101 and plasmid DNA isolated from the obtained transformants was verified by restriction analysis. The plasmid DNA was subsequently transformed to *P. freudenreichii* ATCC6207 as described before. Transformants were selected on erythromycin containing agar plates as described before. The plasmid DNA isolated from the *P. freudenreichii* transformants was verified by restriction analysis.

Shake flask fermentations of pGBP02POB-1 transformants using M1 culture medium and the determination of vitamin B12, adenosyl cobinamide and adenosyl cobinamide phosphate levels were performed as described before.

Ratios of the amount of vitamin B12, adenosyl cobinamide and adenosyl cobinamide phosphate produced per ml culture OD-end-were calculated as described before: The ratio obtained for vitB12 was 19% higher than that obtained for pBRESP36B2p16SH transformants. The ratio obtained for adenosyl cobinamide was 96% lower than that obtained for pBRESP36B2p16SH transformants and no adenosyl cobinamide phosphate could be detected in the pGBP02POB-1 transformants.

EXAMPLE 9

Construction of an Expression Vector for the *Propionibacterium freudenreichii* Genes Encoding Protein B, C and cobA (Hence cob A and U and S) and Its Use For the Production of Vitamin B12 and its Precursors in *Propionibacterium freudenreichii*

In order to over-express simultaneously the genes encoding enzymes B (SEQ ID No.3), C (SEQ ID No.5) and the cobA gene in *Propionibacterium* the three genes were placed behind the 16S rRNA promoter and in front of the hemL terminator as described in the following steps. pGBP02POB-1 was digested with MfeI and BglII and the 1.6 kb fragment was isolated. This fragment was ligated to the 9.7 kb vector fragment of pGBP02COB-1 digested with the same enzymes. After transformation of *E. coli* kanamycin resistant colonies were obtained. The DNA sequence of the cloned fragment was verified through sequence analysis. The resulting construct was named pGBPPOE-1.

pGBP02POE-1 was transformed to *E. coli* JM101 and plasmid DNA isolated from the obtained transformants was verified by restriction analysis. The plasmid DNA was subsequently transformed to *P. freudenreichii* ATCC6207 as described before. Transformants were selected on erythromycin containing agar plates as described before. The plasmid DNA isolated from the *P. freudenreichii* transformants was verified by restriction analysis.

Shake flask fermentations of pGBP02POE-1 transformants using M1 culture medium and the determination of vitamin B12, adenosyl cobinamide and adenosyl cobinamide phosphate levels were performed as described before.

Ratios of the amount of vitB12, adenosyl cobinamide and adenosyl cobinamide phosphate produced per ml culture OD-end were calculated as described before. The ratio obtained for vitB12 was 45% higher than that obtained for pBRESP36B2p16SH transformants. The ratio obtained for adenosyl cobinamide was 65% lower than that obtained for pBRESP36B2p16SH transformants and no adenosyl cobinamide phosphate could be detected in the pGBP02POE-1 transformants.

SUMMARY OF EXAMPLES

The table below displays the experimental data (the empty plasmid values are set to 100% for reference) for the transformed plasmids relative to the empty plasmid control strain)

| Example | Gene | Cobinamide (amount/ ml/OD) | Combinamide P (amount/ ml/OD) | Vitamin $B_{12}$ (amount/ ml/OD) |
|---|---|---|---|---|
| 5 | Empty plasmid | 100 | 100 | 100 |
| 6 | cobA | 227 (+127%) | 300 (+200%) | 94 (−6%) |
| 7 | cobU | 4 (−96%) | 800 (+700%) | 94 (−6%) |
| 8 | cobU and S | 4 (−96%) | 0 | 119 (+19%) |
| 9 | CobA and U and S | 35 (−65%) | 0 | 145 (+45%) |

REFERENCES

1. Sambrook et al. (1989) "Molecular Cloning: A laboratory manual", $2^{nd}$ Edition, Cold Spring Harbor Laboratories, Cold Spring Harbor, New York
2. Innis et al. (1990) "PCR protocols, a guide to methods and applications" Academic Press, San Diego
3. WO-A-99/32617
4. van Zeijl, C. et al. (1998) J. of Biotechnol. 59: 221-224
5. Devereux et al (1984) *Nucleic Acids Research* 12, p387-395
6. Altschul S. F. (1993) J Mol Evol 36:290-300
7. Altschul, S, F et al (1990) J Mol Biol 215:403-10
8. Henikoff and Henikoff(1992) *Proc. Natl. Acad. Sci. USA* 89: 10915-10919).
9. Karlin and Altschul (1993) *Proc. Natl. Acad. Sci. USA* 90: 5873-5787
10. Cunningham and Wells, Science, 244, 1081-1085, 1989
11. de Vos et al. (Science, 255, 306-312, 1992)
12. Smith et al. (J. Mol. Biol.,.224, 899-904, 1992)
13. Wlodaver et al. (FEBS Lett., 309, 59-64, 1992)
14. Ford et al, Protein Expression and Purification, 2, 95-107, 1991
15. Goosen et al, "Transformation and Gene Manipulation in Filamentous Fungi: an overview" in: Handbook of Applied Mycology, Vol. 4 (1992)
16. Romanos et al, Yeast 8:423-488 (1992)
17. R. E. Rose, Nucleic Acids Research 16(1): 355(1988)
18. WO-A-98/04726
19. WO-A-98/30707
20. Alenkso and Clufferbuck, Fungal Genet. Biol 21: 373-397 (1997)
21. EP-A-0,635,574
22. WO-A-98/46772
23. Rapper and Fennell, The Genus *Aspergillus*, The Williams & Wilkins Company, Baltimore, pp 293-344, 1965.
24. B. Cameron et al., J. Bacteriol 171:547-557 (1989)
25. Blanche et al, Angew Chem. Int. Ed. Engl. 34:383-411 (1995)
26. WO-A-97/43421
27. Kiatpapan et al, Applied & Environmental Microbiology 66(11):4688-4695 (November 2000)
28. Kiatpapan & Murooka, Appl. Microbiol. Biotechnol. 56: 144-149 (2001)
29. WO-A-99/67356 (DSM N.V.)
30. Jore et al, Applied and Enviroinmental Microbiol. 67(2): 499-503 (February 2001)
31. EP-A-0184483
32. EP-A-0284603
33. EP-A-0134048
34. EP-A-0253455
35. EP-A-096430
36. EP-A-0301670
37. Bibb et al, Gene 38: 215 (1985).
38. Thompson et al, Gene 20:51 (1982)
39. de Vries et al, J. Gen. Microbiol. 71:515 (1972)
40. Southern, J. Mol. Biol 98: 503 (1975)
41. Roessner et al, Microbiology 148:1845-1853 (2002)
42. Chang et al, Journal of Bacteriology 134(3):1141-1156 (June 1978)
43. Blanche et al, Anal. Biochem. 189:24 (1990)
44. Spalla et al, "Microbial Production of Vitamin $B_{12}$" in: Biotechnology of vitamins, pigments and growth factors, E. J. Van Damme ed., Elsevier, London, New York, pages 257-284.
45. WO-A-98/06868

46. Murakami K, Hashimoto Y, Murooka Y., 1993, Appl Environ Microbiol. 59: 347-350

47. Sattler I, et al. 1995, J Bacteriol. 177:1564-1569.

All documents are herein incorporated by reference.

The invention claimed is:

1. An isolated polynucleotide encoding a synthase or transferase comprising:
   (a) the nucleic acid sequence of SEQ ID NO:5; or
   (b) a nucleic acid sequence having at least 95% identity to SEQ ID NO:5 and encoding a polypeptide from a bacterium of the family *Mycobacteriaceae* using adenosyl-GDP-cobamide as substrate for the biosynthesis of vitamin B12; or
   (c) a nucleic acid sequence encoding the polypeptide of SEQ ID NO:6; or
   (d) a nucleic acid sequence which hybridizes under high stringency conditions of 0.3 M sodium chloride and 0.03 M sodium citrate at 60° C. to a sequence as defined in (a), (b), or (c).

2. The polynucleotide according to claim 1 which comprises:
   (a)
      (1) the coding sequence of SEQ ID NO:5 or
      (2) a sequence which hybridizes under high stringency conditions of 0.3 M sodium chloride and 0.03 M sodium citrate at 60° C. to the complement of the sequence defined in (1); or
   (b) a sequence complementary to the coding sequence of SEQ ID NO:5.

3. The polynucleotide according to claim 1 which is a DNA sequence.

4. A vector comprising one or more polynucleotide sequence(s) according to claim 1.

5. The vector according to claim 4 which is an expression vector.

6. An isolated host cell which comprises at least one polynucleotide according to claim 1, or has multiple copies of one or more of the polynucleotide(s).

7. An isolated host cell which comprises, as a heterologous sequence, a polynucleotide according to claim 1.

8. An isolated prokaryotic host cell transformed with a vector comprising the polynucleotide according to claim 1.

9. A process of producing or synthesizing a polypeptide, comprising:
   (a) culturing a host cell as defined in claim 8 under conditions that provide for expression of the polypeptide and
   (b) isolating said polypeptide.

10. The vector according to claim 4 which further comprises:
   (a) a polynucleotide encoding a polypeptide wherein said polypeptide has the amino acid sequence of SEQ ID NO:4 or has at least 95% identity to the amino acid sequence of SEQ ID NO:4, or the nucleic acid sequence SEQ ID NO:3; and
   (b) a polynucleotide encoding a polypeptide wherein said polypeptide has the amino acid sequence of SEQ ID NO:6 or has at least 95% identity to the amino acid sequence of SEQ ID NO:6, or the nucleic acid sequence SEQ ID NO:5.

11. The vector according to claim 4 further comprising a nucleic acid sequence encoding a CobA protein.

12. The vector according to claim 5 wherein the polynucleotide is a DNA sequence operably linked to a regulatory sequence.

13. A process for the preparation of an amine, comprising contacting a substrate with a host cell as defined in claim 6.

14. A process for the preparation of a phosphate-containing compound, comprising contacting a substrate with a host cell as defined in claim 6.

15. A process for the preparation of a nucleotidyl-containing compound, comprising contacting a substrate with a host cell as defined in claim 6.

16. A process for the preparation of an aryl-containing compound, comprising contacting a substrate with a host cell as defined in claim 6.

17. A process for the preparation of an adenosine-containing compound, comprising contacting a substrate with a host cell as defined in claim 6.

18. The vector according to claim 4 which further comprises:
   (a) a polynucleotide encoding a polypeptide wherein said polypeptide has the amino acid sequence of SEQ ID NO:4 or has at least 95% identity to the amino acid sequence of SEQ ID NO:4, or the nucleic acid sequence SEQ ID NO:3; and
   (b) a polynucleotide encoding a polypeptide wherein said polypeptide has the amino acid sequence of SEQ ID NO:6 or has at least 95% identity to the amino acid sequence of SEQ ID NO:6, or the nucleic acid sequence SEQ ID NO:5 and further comprising a nucleic acid sequence encoding the CobA protein.

19. The polynucleotide according to claim 1 which further comprises:
   (a) the nucleic acid sequence of SEQ ID NO:3; or
   (b) a nucleic acid sequence having at least 95% identity to SEQ ID NO:3; and encoding a polypeptide from a bacterium of the family *Mycobacteriaceae* using adenosyl cobamide and/or adenosyl cobamide phosphate as substrate for the biosynthesis of vitamin B12; or
   (c) a nucleic acid sequence encoding the polypeptide of SEQ ID NO:4; or
   (d) a nucleic acid sequence which hybridizes under high stringency conditions of hybridization in 0.3 M sodium chloride and 0.03 M sodium citrate at 60° C. to a sequence as defined in (a), (b), or (c).

20. A vector comprising one or more polynucleotide sequence(s) according to claim 19.

21. An isolated host cell which comprises at least one polynucleotide according to claim 19 or has multiple copies of one or more of the polynucleotide(s).

22. An isolated prokaryotic host cell transformed with a vector according to claim 20.

23. A process of producing or synthesizing a polypeptide, comprising:
   (a) culturing a host cell as defined in claim 22 under conditions that provide for expression of the polypeptide and
   (b) isolating said polypeptide.

24. The isolated polynucleotide according to claim 1 encoding a polypeptide having cobalamin (5'-phosphate) synthase activity [EC 2.7.8.-].

25. The polynucleotide according to claim 19 wherein the further comprised polypeptide has cobinamide kinase activity [EC 2.7.1-] and/or cobinamide phosphate guanyl transferase activity [EC 2.7.7.-].

26. The vector according to claim 4 which further comprises:
   (a) a polynucleotide encoding a polypeptide wherein said polypeptide has the amino acid sequence of SEQ ID NO:4 or has at least 95% identity to the amino acid sequence of SEQ ID NO:4, or the nucleic acid sequence SEQ ID NO:3; and
   (b) a polynucleotide encoding a polypeptide wherein said polypeptide has the amino acid sequence of SEQ ID NO:6 or has at least 95% identity to the amino acid sequence of SEQ ID NO:6, or the nucleic acid sequence SEQ ID NO:5.

27. The vector according to claim 20 further comprising a nucleic acid sequence encoding a CobA protein.

* * * * *